(12) United States Patent
Collins

(10) Patent No.: US 10,232,371 B2
(45) Date of Patent: Mar. 19, 2019

(54) MICROFLUIDIC DEVICES AND METHODS FOR CELL PROCESSING

(71) Applicant: John Collins, Irvine, CA (US)

(72) Inventor: John Collins, Irvine, CA (US)

(73) Assignee: Biopico Systems Inc, Irvine, CA (US)

(*) Notice: Subject to any disclaimer, the term of this patent is extended or adjusted under 35 U.S.C. 154(b) by 595 days.

(21) Appl. No.: 14/808,703

(22) Filed: Jul. 24, 2015

(65) Prior Publication Data
US 2016/0167051 A1 Jun. 16, 2016

Related U.S. Application Data

(62) Division of application No. 13/738,968, filed on Jan. 10, 2013, now Pat. No. 9,149,806.

(51) Int. Cl.
| | |
|---|---|
| *B01L 3/00* | (2006.01) |
| *G01N 15/02* | (2006.01) |
| *G01N 15/10* | (2006.01) |
| *G01N 33/483* | (2006.01) |
| *C12N 5/074* | (2010.01) |
| *B01L 7/00* | (2006.01) |

(52) U.S. Cl.
CPC ... *B01L 3/502761* (2013.01); *B01L 3/502753* (2013.01); *C12N 5/0696* (2013.01); *G01N 15/1031* (2013.01); *G01N 15/1056* (2013.01); *G01N 33/4833* (2013.01); *B01L 7/52* (2013.01); *B01L 2200/0652* (2013.01); *B01L 2200/0668* (2013.01); *B01L 2200/0673* (2013.01); *B01L 2300/0832* (2013.01); *B01L 2300/0861* (2013.01); *B01L 2300/0864* (2013.01); *B01L 2300/0883* (2013.01); *B01L 2300/1822* (2013.01); *B01L 2400/086* (2013.01)

(58) Field of Classification Search
None
See application file for complete search history.

(56) References Cited

FOREIGN PATENT DOCUMENTS

CN 102162815 A * 8/2011

OTHER PUBLICATIONS

Kuntaegowdanahalli et al., "Inertial microfluidics for continuous particle separation in spiral microchannels," Lab Chip 2009, 9:2973-2980.*

* cited by examiner

*Primary Examiner* — Kaijiang Zhang

(57) ABSTRACT

Microfluidic devices and methods that use cells such as cancer cells, stem cells, blood cells for preprocessing, sorting for various biodiagnostics or therapeutical applications are described. Microfluidics electrical sensing such as measurement of field potential or current and phenomena such as immiscible fluidics, inertial fluidics are used as the basis for cell and molecular processing (e.g., characterizing, sorting, isolation, processing, amplification.) of different particles, chemical compositions or biospecies (e.g., different cells, cells containing different substances, different particles, different biochemical compositions, proteins, enzymes etc.). Specifically, the present invention discloses a number of sorting schemes for stem cells, whole blood and circulating tumor cells, and extracting serum from whole blood.

15 Claims, 30 Drawing Sheets

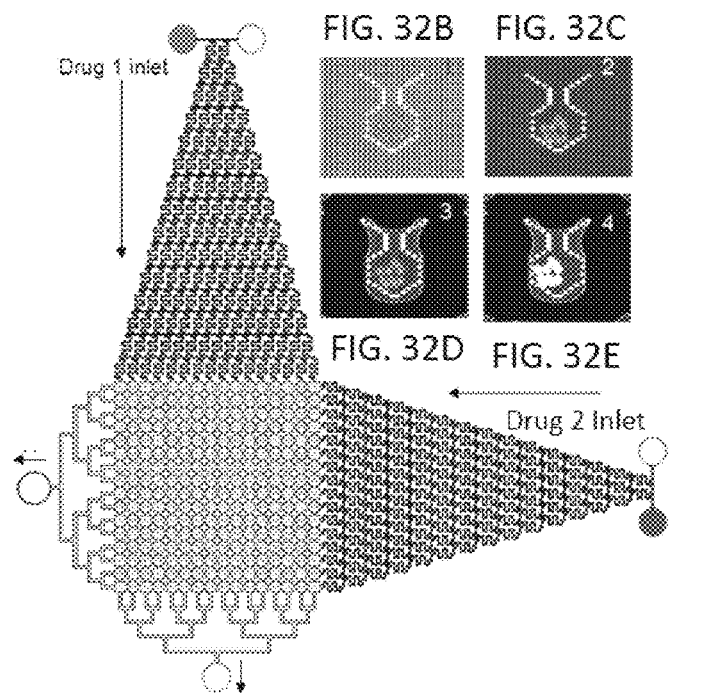
FIG. 32A
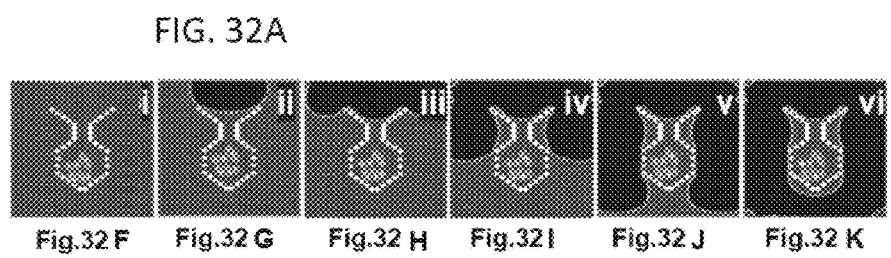
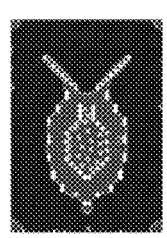

MICROFLUIDIC DEVICES AND METHODS FOR CELL PROCESSING

This is a divisional of non-provisional patent application entitled "Microfluidic Devices and Methods for Cell Sorting, Cell Culture and Cells Based Diagnostics and Therapeutics," Ser. No. 13/738,968 filed on Jan. 10, 2013, which claims the benefit of and priority to provisional patent application Ser. No. 61/585,181 filed on Jan. 10, 2012. The contents of the above-mentioned applications are hereby incorporated fully by reference into the present application.

STATEMENT OF GOVERNMENT INTEREST

This invention was made partly (iPS Cells sorting) with Government support under Contract No. W81XWH-12-C-0108 awarded by DoD and NIH. The Government has certain rights in this invention.

BACKGROUND

The present application relates generally to medical devices and methods and more particularly to microfluidic devices and methods for processing cells and molecules for therapeutics (stem cell therapy, gene therapy) and diagnostics (e.g., characterizing, amplification, sensing, processing, enriching circulating tumor cells.) using different biospecies (e.g., different cells, cells containing different substances, different particles, different biochemical compositions, genes, proteins, enzymes etc.).

'On-the-Fly Field-Potential Sensing Electrode Track' Technology for Stem Cell Sorting The derivation of patient-specific reprogrammed somatic cells makes immunologically compatible stem cell replacement strategy very attractive for several applications such as spinal cord therapy. Pluripotency has been derived at increased efficiencies from several easily accessible human cell types, including blood cells, keratinocytes and dermal fibroblasts enable drug screening, disease modeling and autologous cell transplantation in clinical therapy. The major challenge in this tissue replacement therapy is the establishment of effective isolation of differentiated cells to avoid teratoma formation. However, at present, it is unclear whether any of the currently available strategies to generate differentiated cells from iPSCs is able to eliminate the risk of teratoma formation. Moreover, the current separation method—microscope-assisted manual isolation—is error-prone, time-consuming, and labor-intensive, and does have the capacity to sort multiple cell phenotypes. Fluorescence-activated cell sorting is capable of sorting multiple phenotypes but uses labeling of cells. Magnetic-activated cell sorting also lacks the robustness to sort out more than one cell type at a time. Unfortunately, conventional separation techniques requiring exogenous labeling or genetic modification is not suitable for clinical applications and so superior iPSC sorting is an urgent unmet need. The novel flow based high throughput label-free sorting scheme to separate stem cells and their differentiated progeny for regenerative medicine using cell sorting based on their response to electrical stimulation called 'On-the-Fly Field-potential Sensing Electrode Track' (OFFSET) technology is significant.

This high throughput integrated OFFSET platform can be configured to:
  precisely flow and focus high throughput single-cells
  accurately detect single cells using impedance sensing
  stimulate the detected cells triggered by the impedance sensor
  detect their stimulated response through an electrode array
  process the stimulus response signature in real time
  perform fluidic switching with the comparison of pre-stored stimulus response signatures In microfluidics, surface electrodes have been used to detect electrical signals from cells such as extracellular ionic currents producing a characteristic field potential (FP) signal in different ion channels and gating kinetics. Though these electrophysiological measurements have been used to identify subpopulations of electrically-excitable cells, at static conditions, high throughput flow based 'on the fly' recording have not done so far which are very essential for clinical applications. These FP signals can be monitored during stem cell differentiation and are characterized as a marker for endpoint analysis of embryonic stem cells in order to quantify ion channel expression levels and cell maturity or phenotype. Our innovation is to develop a flow based system to sense the degree to which stem cells have differentiated into these cell types using 'On-the-Fly Field-potential Sensing Electrode Track' (OFFSET) technology. Therefore OFFSET technology offers a label-free cell sorting of stem cells and their differentiated progeny based on their response to electrical stimulation with several advantages. In potential therapeutic applications, the cell populations relevant for therapy can be electrically excited and the resulting transmembrane ion currents are measured using an array of surface microelectrodes along the direction of the flow. The electrical current measurements in response to electrical stimulation for differentiated states of the cells are built up as electrical signatures for real time comparison and sorting. Since these transmembrane ion currents are measured non-invasively to sort the differentiated cells based on these field potential markers, the sorted cells are highly viable for therapeutic applications. Therefore ventricular-like cardiomyocytes from iPSC derived populations can be separated for cardiac tissue replacement therapies in an 'on the fly' system at high throughput scale. These cell populations for such sorting include cardiomyocytes, neurons, skeletal muscle, and vascular smooth muscle. The OFFSET platform combines the technologies of flow based field potential sensing, high speed signal processing and high throughput microfluidic cell sorting to rapidly detect, identify, and sort millions of specific cells for downstream applications. Our endeavor to overcome the barriers that prevent successful translation of stem cell biology into clinical therapy is highly significant to improve human health and control of human diseases.

Flow Driven Blood Based Sorting of Cancer Cells Using Multi Spiral Fluidic Channels Sorting of cancer cells particularly circulating tumor cells (CTCs) from blood is important for clinical diagnostics. Despite the progress in early diagnosis and introduction of new therapy regimes, cancer remains a prominent health concern in modern societies with one in four deaths in the US and a total of 1,529,560 new cancer cases with 569,490 deaths from cancer projected in 2010. The early dissemination of the cancer and the systemic spread of tumor cells to other parts of the body results in a negative prognosis and death. Such CTCs can be found in the peripheral blood of patients before the primary tumor is detected. Therefore CTCs are fluid biopsy for primary tumor cells sampled as a minimally invasive, prognostic and predictive marker to reflect the biological characteristics of tumors and are implemented in an increasing number of clinical studies. These CTCs play a pivotal role in changing the biology and marker expression compared with the primary tumor and so detection and characterization of these cells are believed to have a substantial clinical impact on the prognosis and optimal disease management of cancer patients. In addition to a potential role in early diagnosis and prognosis, the detection of CTCs can guide therapeutic strategies for personalized treatment of patients with metastatic cancer. Identification, enumeration and characterization of CTC through immunocytochemistry, fluorescence in situ hybridization assays and all relevant molecular techniques. However, the most challenging obstacle in the separation and detection of CTCs is their extremely low concentration. Due to the rarity of the CTCs, existing immunomagnetic cell separation techniques lack the ability to separate all types of CTCs directly from whole blood at rapid and low cost.

Quantification of CTCs through the use of magnetic bead-conjugated antibodies against epithelial-cell adhesion molecule (EpCAM) remains a point of discussion for treatment decisions. EpCAM-dependent assays are based upon the assumption that the presence of epithelial cells in peripheral blood indicates the presence of tumor cells. However, epithelial cells may be found in healthy donors and EpCAM-based assays are not able to detect normal-like tumor cells. Moreover, certain tumor types such as melanoma are not of epithelial origin which suggests that EpCAM-based assays may be of limited use. Epithelial antigen may be lost on CTCs due to the epithelial-mesenchymal transition (EMT), which is considered to be a crucial event in the metastatic process. Furthermore, CTCs must be isolated alive for testing their potential capacity to initiate tumor formation in animal models and must become easily accessible to a large range of molecular biological analysis. Therefore flow driven blood based inexpensive on-chip high performance sorting using yoked channels (f-BIOPSY) system that can isolate, quantify, and analyze circulating tumor cells from a blood sample under inertial fluidics conditions using successive approximation sorting method is of great significance. The f-BIOPSY system as compared in Table 1 can prepare CTCs for analyzing relevant cellular and molecular biological techniques for potential genetic abnormalities without using an antibody based assay. The f-BIOPSY system could have a profound influence on the early diagnosis, prognosis, early detection of relapse, and the development of new targeted strategies.

TABLE 1

Comparison of f-BIOPSY technology

| Characteristics | Veridex (Cell Search) | Xanapath (I-SCOPE) | Biopico (f-BIOPSY) |
|---|---|---|---|
| Throughput | Low | Medium | High |
| Specificity | Low | Low | Medium |
| Integration | Low | Low | High |
| Fluid handling | Required | Required | Not required |
| Sorting/Enrichment | Immuno-magnetic | Immuno-magnetic | Inertial fluidics |
| Multiplexity | Low | Low | High |
| Cell viability | Low | Low | High |

In the f-BIOPSY device, blood flow passes through a "yoked" spiral channel using successive approximation method, allowing size-selective isolation of rare tumor cells under fully reproducible and standardized inertial fluidics conditions. The f-BIOPSY device is a low-cost innovative technology with the aim of achieving isolation of tumor cells without the requirement for large and expensive apparatus and is compared with other leading systems in Table 1. Compared previous spiral method, the clinically usable highly innovative f-BIOPSY system has several advantages as characterized in Table 2. The cells isolated from the device are can be analyzed using all relevant cellular and molecular biological techniques pertinent to the identification and characterization of CTCs and their potential genetic abnormalities. This label free system can isolate living cells, allowing further tissue culture experiments. The goal of this cell sorting system is to avoid harming the cells during sorting so that high performance multianalyte detection using mRNA expression profiling can be achieved. Furthermore, tumor cells can be isolated without using an epithelial antibody-based assay, suggesting that the f-BIOPSY device can be used for the isolation of a large spectrum of tumor cells, including cells of non-epithelial origin. They can be used within clinical trials as a basis for early therapy stratification and monitoring to replace expensive and adverse radiological imaging techniques. The f-BIOPSY technology can be sensitive and reliable to allow detection and analysis of CTCs routinely for the early diagnosis, risk stratification in the adjuvant setting, early detection of relapse, the development of new targeted strategies and guiding treatment decisions.

TABLE 2

Innovation of f-BIOPSY System

| Specification | Previous Method | f-BIOPSY System |
|---|---|---|
| Spiral | Single spiral | Double spiral or multiple spirals |
| Width | Constant | Decreasing on one spiral and increasing on other |
| Main channel | Simple channel | Expansion structures in main channel |
| Sample concentration | RBC and leukocytes are sorted out at the end the channel | Continuously RBC and other cells are extracted out in by-pass channels from one spiral to another spiral channels |
| Sorting efficiency | Inefficient | Efficient due to increasing channel width |
| Multianalyte sorting | Not accurate | Cascaded branched spiral channels with defined geometry enable multianalyte sorting |
| Rapid sorter | constant width makes slow sorting | Larger effective width of parallel spiral channels enables high flow rate sorting. |

Serum Based Mobile Driven Analyzer for Rapid Tests

The advent of personalized diagnostic approaches demands highly flexible analytical devices to perform multiplexed analysis for determining a wide range of disease biomarkers such as enzymes, antigens and nucleic acids and therapeutic agents. In this regard, lab-on-chip microfluidic devices paved the way for miniaturized, self-standing analytical systems and technological solutions for integration, multiplexing and programming of such biospecific reactions. Panel assays with "ad hoc" biomarkers for monitoring the health status and the drug efficacy in a specific patient is an urgent need for these devices. With this respect, these devices could be operated by a patient, a nurse, a physician or a technician directly in the doctor's office or at the patient's bed to rapidly provide all the clinical chemistry information necessary for accurate diagnosis and patient follow-up. With the increasing power of computation, communication and versatility of smart phones, in recent times, it is useful to configure the smart phones with fluidic devices for point of care diagnostics. However, performing such rapid blood based diagnostics would require development of appropriate technologies for preprocessing blood and measurement for personalized assays. Therefore, Serum based Mobile driven Analyzer for Rapid Tests (SMART) is of great significance. This effort can separate serum from whole blood, to perform diagnostics and to interface with smart phone to tap its power through cloud computing and making the diagnostics information available in private networks for its better utilization. In this system, personal diagnostics information from whole blood is derived using a microfluidic chip and transmitted to cloud computing network for access to relevant users. The innovations are as follows:

1. The SMART system can utilize a rapid serum sorting scheme for colorimetric diagnostics of test panels from serum.
2. Rapid pumping of serum in the SMART system is accomplished by acoustic steaming driven integrated passive pump.
3. Colorimetric measurement imaging is accomplished by integrated lensless optics so that compact smart phone camera can be utilized for quantification.
4. Computation, analysis and communication of the diagnostics data to a cloud computing system is enabled by the smart phone for remote multiuser access.

The innovations in SMART system combines the technologies of serum separation in spiral fluidic channel, acoustic cavitations streaming pump, colorimetric assay for test panels, smart phone based imaging and health information communication through cloud computing to develop a powerful platform for space exploration related point of care diagnostics and commercialization. The system could carry out in a quick, multiplex diagnostics in a cost-effective fashion for crew health monitoring and clinical diagnostic or therapeutic purposes. As an example, simultaneous quantitative analysis of glucose, lactate, and uric acid in blood samples is applied.

The device allows short analysis time due to miniaturization and high flexibility of assay and format, as well as a potential costs reduction. Its key advantage is that the different types of assays described above can be performed simultaneously exploiting microarray configurations. This multiplexing capability can permit the development of chips for the detection of panels of diagnostic biomarkers, e.g., for performing the diagnosis of an infectious disease by detecting both the pathogen nucleic acids and the host antibodies produced in response to the infection or to assess the liver function by combining routine clinical chemistry analyses (bilirubin, cholesterol) with the measurement of serum enzyme activities (alkaline phosphatase, aspartate, and alanine aminotransferase) and the detection of a present or past hepatitis viral infection. Thanks to the flexibility of chip fabrication, chips to evaluate panels of biomarkers could be also specifically developed for a given patient to perform "personalized medicine" on the basis of genetic approaches.

Parallel Incubators with Loaded Single Cells for Lysis and Amplification Reactions While the cell is recognized as a fundamental unit that can generate a complex organism containing cells with diverse patterns of gene expression, only a limited number of measurement techniques permit single cell resolution that is interesting to the biological, medical, and pharmaceutical communities. Traditional methods of gene expression analysis examine pooled mRNA from thousands of cells, resulting in an averaged picture of gene expression across an entire cell population. This restricts the ability to distinguish between the individual responses inherent cell-cell heterogeneity within a sample and to disentangle the complexity of the regulatory mechanisms controlling specific responses. The primary problems that hinder such single cell analyses are difficulty in handling a minute amount of sample, inability to prepare and manipulate single cells, inability to have high-throughput capability, and not being able to integrate with amplification protocols and detection mechanisms. Further, the application of current single cell PCR techniques is limited by long turnaround times, high cost, labor intensiveness, the need for special technical skills, and/or the high risk of amplicon contamination. The need for single-cell mRNA analysis is evident given the vast cellular heterogeneity of all tissue cells and the recent developments in whole genome amplification procedures, single-cell complementary DNA arrays and single-cell comparative genomic hybridization. When genetic analysis of single cells becomes a common practice, new possibilities for diagnosis and research can open up. Current attempts to perform high-throughput single cell dispensing and analysis involves flow cytometry and robotics. However, such systems are expensive as a routine research or diagnostic device. Therefore, Biopico Systems, Irvine identified this opportunity to develop a 'Parallel Incubators with Loaded single cells for Lysis and Amplification Reactions (PILLAR)' system to perform high-throughput quantitative single-cell gene expression profiling. This system can provide unique information critical not only to the quality control and clinical translatability of iPSCs for regenerative medicine but also to understand the relationship between transcriptional and phenotypic variation in the development of pathology, oncogenesis, and other processes of a target cell. For example, precise molecular analysis of abnormal gene and proteins in single cells from a large population of cells helps in cell clonality, genetic anticipation, single-cell DNA polymorphisms and early diagnosis of cancer, infectious diseases and prenatal screening.

PILLAR technology, first traps single cells at configured micropillars and then encapsulates using immiscible fluidics around the single cell traps as picoliter reservoirs. The novelties pertaining to the development of the PILLAR system include 1) trapping of single cells with a set of micropillars (and guiding pillars for focusing the cells towards traps) 2) formation of microreactors using immiscible fluids around a single cell and 3) thermocyling of these anchored microreactors using flow of oil at two different temperatures for fast and reliable PCR reaction. The all-in-one PILLAR system combines commercially available fluorescent RT-PCR with immiscible microfluidics and single cell microtrapping technologies for performing thousands of single cell RT PCR in picoliter volumes in a quick, high-throughput, and cost-effective fashion. The PILLAR system can help to understand the relationship between stochastic variations of gene expression within individual cells and heterogeneous transcriptional profiles across a population of cells.

This highly integrated PILLAR platform is configured:
to precisely trap high throughput single-cells in array of micropillar based trapping sites
to encapsulate single cells as picoliter reactors by flow of immiscible fluids
to rapid thermal cycling on anchored single droplets at the micropillar trapping sites
to perform thousands of single-cell PCR for regenerative medicine or clinical diagnostics This PILLAR platform would be very useful for accurately quantifying the differentiation process and could serve as a performance metric of every step of stem cell differentiation process for regenerative medicine. The combination of high-fidelity manipulation of single cells and the ability to perform nucleic acid amplification offers the possibility of developing a powerful automated instrument which has highly significant commercial applications such as cancer diagnostics and prenatal diagnostics.

Biochemical analysis of genes and proteins from single cells is of significant interest. The intellectual merit of the technology is to develop a chip/system that entraps single cells and performs 10,000 parallel single cell RT-PCRs simultaneously in a cost-effective fashion. This can provide a means to perform precise molecular analyses on single cells from large populations of cells using a highly sensitive approach. The chip combines three unique microfluidic techniques for the automation of a cell-based real-time PCR-based diagnostic system on a chip with supporting analytical instrumentation. This novel device can differentiate gene expression of a particular rare cell from other single cells with a capability of multiplexing for the detection of house-keeping genes and target genes. This capacity to analyze large populations of individual cells could provide unique opportunities in the life sciences and support biomedical research activities in the fields of virology, oncology and pathology.

The broader/commercial impact of the project is the development of a cost-effective solution for diagnosis of various diseases using cellular gene expression variation of multiple single cells for leukemia, prenatal screening, genetic screening of multiple diseases, or the detection of viruses such as HIV virus. Isolation of single cell in a high throughput fashion followed by gene expression analysis can lead to several research findings. Such findings can lead to early detection and prognosis of diseased states including differential detection of an infected cell from uninfected cells, detection of cancer markers in different cells, and changes in gene expression of diseased single cells at high speed and high specificity. Further, small concentration changes and/or altered modification patterns of disease-relevant components, such as mRNA and/or micro RNA, have the potential to serve as indications of the onset, stage, and response to therapy of several diseases. In current, manual, single-cell PCR methods low abundance mRNA is often lost during cell lysis and extraction processes and these methods are also extremely labor intensive requiring expensive equipment to isolate single-cells to perform PCR. The PILLAR system can detect rare abnormal cells and carry out single-cell PCR or RT-PCR. Micrototal analysis systems of the prior art have typically involves microdroplets formation followed by cells and molecules encapsulation. These technologies require external active instruments to accomplish medical diagnostics which can be difficult to perform one touch or one step device operation. On the other hand, in our technology, single or multiple cells or molecules are trapped first either at configured micropillars or nozzles and then picoliter volume reservoirs or reactors are formed around the single cell using immiscible fluidics. The isolated single cell or cells or molecules are processed for multistep temperature reactions or chemical reaction. Multiple temperature biochemical reaction such as PCR or linear isothermal amplification can be carried out on the trapped picoreactors by flowing immiscible fluids such as oil around the picoreactors. Further, if needed, a slip and lock chip technique supplies additional reagent from another layer of microfluidic chip. PCR using fluid flow thermal cycling is also highly innovative. The dimensions of the pillars for trapping cells and flow rate of the oil for encapsulating single cells are optimized for the efficiency and specificity of the diagnostics device.

Programmable Array of Living Cells for Combinatorial Drug Screening

Combinatorial drug screening for cell based drug discovery and efficacy is increasingly dependent on high-throughput technologies due to the need for more efficient screening of multiple combinatorial drug candidates. Massively parallel analytical screening technologies are needed for the exploitation of biological insight in the oncology clinic since cellular responses to anti-cancer modalities have been stochastic in nature. Miniaturized reactors have been developed to reduce culture volume, increase process efficiency and to administer chemotherapeutic drugs sequentially or together in combination for massive experimental parallelization of real-time drug screening routines. The use of combination therapies can lead to increased efficacies at significantly lower doses and side-effects and so investigation of combination therapies for curative and palliative care is very significant. Therefore an automatic Programmable Array of Living cells (PAL) that integrates on-chip generation of drug concentrations and pair-wise combinations with parallel culture of cells is significant for drug candidate screening applications.

SUMMARY

In accordance with the present invention, there are provided methods for stem cell sorting using flow based field potential sensing and sorting, circulating tumor cell sorting using multiple spiral channels, cell culture using on-chip pump and cell based assays in microfluidics, blood serum separation for smart phone based diagnostics, multiplexed single cell PCR using multiple pillars and immiscible fluidics In accordance with the stem cell sorting invention three sets of electrodes are employed for impedance sensing, stimulus current and discrete recording of time domain stimulus response using an array of electrodes (20 pairs or more) in the path of flow cells in order to distinguish between undifferentiated cells and different differentiated species. Still further in accordance with the present invention, there are provided methods for the extraction of sheath fluid flow from dilution of the sorted cells and deflecting fluidic inlets for high speed sorting using high pressure fluidic pulse.

In accordance with the circulating tumor cells sorting invention, there are provided methods employing a spiral microfluidic channel system having one or more spiral microfluidic channels with periodically interconnected channels called "yoked channels". Cells are delivered at an inlet, then flowed through a primary spiral microfluidic channel and one or more secondary spiral microfluidic channels, and collected at one or more outlets. For example, CTCs can be separated from a blood sample having, among other cells, erythrocytes, leukocytes and CTCs using the spiral microfluidic channel system.

Still further in accordance with the present invention, there are provided methods with one or more spiral microfluidic channels with width gradients. Such method can have decreasing width gradient periodic pinching regions to sort cells at high efficiency. While one spiral channel can have decreasing width gradient, another may have increasing width gradient in order to provide balanced pressure profile. For example, a primary spiral microfluidic channel has a greater width at its inlet than at its outlet, while a secondary spiral microfluidic channel has a smaller width at its inlet than at its outlet.

Still further in accordance with the present invention, there are provided methods with connecting channels (yoked channels or interconnect channels) between two successive and concentric spiral microfluidic channels whose widths depend on the size of the cells or particles or species under sorting.

Still further in accordance with the present invention, there are provided methods with periodic pinching regions whose length depends on the flow rate of the fluidics. The lengths of the pinching regions are also increasing from the center of the spiral microfluidic channel system towards outlets of the spiral microfluidic channels.

Still further in accordance with the present invention, there are provided methods for off-chip pre-processing and on-chip processing of cells.

Still further in accordance with the present invention, there are provided methods using multiple species sorting with multistep for separating different species of blood and for isolating CTCs of overlapping sizes with the peripheral blood leukocyte size scale.

In accordance with the serum based smart phone driven diagnostics invention, there are provided methods for separating serum from whole blood using dual spiral channels. In one channel serum is separated due to geometric singularity at the dead zone and is transferred to the adjacent spiral channel through connecting channels.

Still further in accordance with the present invention, there are provided methods for clinical diagnostics using colorimetric assay or fluorescent assay or other spectroscopy to perform serum based multistep chemistry on microarray spots in cellulose pad, image microarray spots using extended optics on smart phones, quantify the assay using image processing and transmit the results to cloud computing server for healthcare providers or other personals.

Still further in accordance with the present invention, there are provided methods for integrating software for optics, imaging and mechanical hardware, software for communicating to cloud portal, software for image processing, software for phone application and interaction with users.

Still further in accordance with the present invention there are methods provided for extraction of serum from blood using multiple spiral channels In accordance with the single cell PCR invention, there are provided methods for encapsulation of cells or molecules in trapping sites such as configured micropillars or micronozzles using immiscible fluids such as oil, fluorinert, oil containing surfactants, gel or other medium.

Still further in accordance with the present invention, there are provided methods for multistep thermal cycling for PCR or other amplification by flowing of immiscible fluids as mentioned about at different temperature.

Still further in accordance with the present invention, there are provided methods for performing multistep chemical reaction using modified slipchip.

Still further in accordance with the present invention, there are provided methods for fabrication of the chips with microarray dried spots of primers or any other reagent or immobilized on semi-spherical gel on one layer and trapping of single cells with 6 sets of configured micropillars in another layer Still further in accordance with the present invention, there are provided methods for the assay system for diagnostics in frequency domain by performing thousands of biochemical reactions and counting the positives for the quantification.

Still further in accordance with the present invention, there are provided methods for performing additional movement of trapped picoreactor droplet using electrowetting on dielectric.

Still further in accordance with the present invention, there are provided methods for carrying out electrophoresis in the medium of gel based immiscible fluids.

Still further in accordance with the present invention, there are provided methods for preprocessing samples such as blood, tissue, tumors etc using cascaded magnetodiffusion or compounded flow focusing spiral inertial microfluidic based cell sorting.

Still further in accordance with the present invention, there are provided methods for the formation of single cell encapsulated droplets or various molecules encapsulated droplets undocked from the trapping sites for further processing.

Still further in accordance with the present invention, there are provided methods for separation or purification of constituents of the droplets such as mRNA or other species using magnetic beads through multistep processing of droplets such as cascaded fusion and fission steps.

Still further in accordance with the present invention, there are provided microfluidic devices for carrying out the above-summarized methods.

A microfluidic device according one implementation of the present invention generally comprises a) at least six set of micropillars in a configuration to trap cells electrodes positioned parallel to the direction of flow, b) apparatus (e.g., on chip pump or micropumps) for applying a flow for oil and aqueous fluids and c) apparatus for measuring the biochemical reaction (e.g., fluorescent microcope, integrated fluorescence reader, other optical reader, GMR sensor, impedance sensor, nanosensor). (d) pair of electrodes to carry out electrophoresis in gel after amplification of molecules or genes (e) This device may comprise a microfluidic device that has a substrate layer and an upper layer, wherein the electrodes are located (e.g., fabricated, formed, affixed to or otherwise disposed on or in) one of the layers (e.g., on the substrate layer) and the microchannel is located (e.g., fabricated, formed, affixed to or otherwise disposed on or in) in the other layer (e.g., in the upper layer). The layers of the device may be fully or partially formed of different materials. For example, the layer in or on which the electrodes are located (e.g., the substrate layer) may comprise a glass and the layer on or in which the microchannel is located (e.g., the upper layer) may comprise a suitable polymeric material such as polydimethylsiloxane (PDMS), polycarbonate, polyacrylate, COC etc.

Still further in accordance with the present invention, there are provided methods for transporting samples and reagents using electrowetting on dielectric actuation in nanodroplets.

Still further in accordance with the present invention there are methods for encapsulating single or multiple cells along with nutrients and media and label molecules in different reactors and monitoring their growth using fluorescence or electrical impedance or any other methods.

Further aspects, elements and details of the present invention are described in the detailed description and examples set forth here below.

BRIEF DESCRIPTION OF THE DRAWINGS

FIG. 32A-32L Schematic diagram of a programmable array of living cells system. Full Chip Diagram. Fluidic operations of the chip are illustrated in the in the in-pictures. Flow of cells through the chip to trap cells at the 'cup' shaped reactor till it overflows. Flow of buffer to clean up the cells in the channels and incubate for 24 hours. Flow of combinatorial drug as a 2-D. Flow of oil to form cells encapsulated reactors in isolation. Cell culture for 24 hours with Florescence imaging of cell growth monitoring every 6 hours. Time lapse frames of aqueous cells in compartments isolation by virtual walls are shown. Alternate diagram featuring complete isolation of cells from immiscible fluidics is shown.

DETAILED DESCRIPTION AND EXAMPLES

Figure 1A:
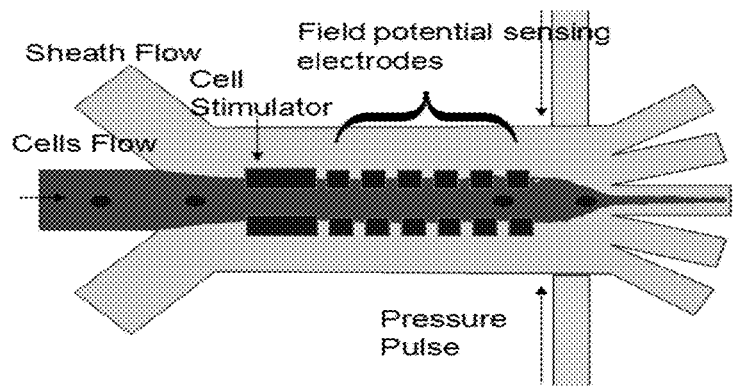
FIG. 1A-1B Schematic configuration of the stem cell sorting fluidic and electrodes array system. Representation of electrode array for impedance sensing, stimulus current and discrete recording of time domain stimulus response using 20 electrodes in the path of flow cells.
Figure 1B:
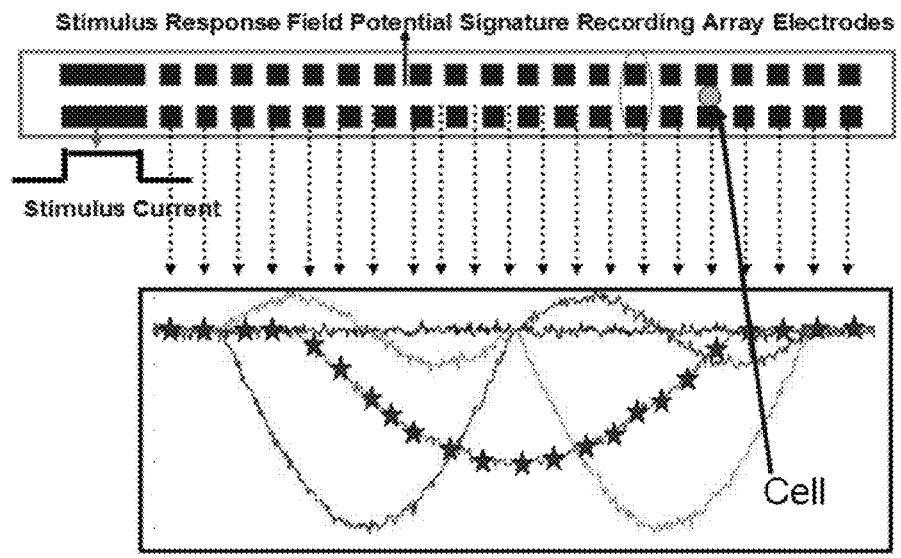

'On-the-Fly Field-Potential Sensing Electrode Track' Technology for Stem Cell Sorting The OFFSET disposable chip (shown in FIG. 1A) utilizes sheath flow fluidics, single cell impedance sensing, on the flow stimulation and recording of response from individual cells and flow switching microfluidics for rapid sorting thousands of iPSC. The chip includes (a) sheath flow inlets, (b) impedance sensor electrodes, (c) stimulus current electrodes, (d) array of stimulus response recording electrodes (e) fluidic switching outlets. In the OFFSET chip has channel of width 50 um and height 20 um with three inlets and 5 outlets and a 24 pairs of Pt or Au electrodes on glass substrate with a distance of 50 um between the electrodes. The first pair of electrodes for impedance measurement is 50 um wide while the stimulation electrode is fabricated to be 500 um so that each cell can stay at the stimulated field for 5 ms. The flow rate of the cells flow can be considered to be at a velocity of 0.1 m/s. FIG. 1B shows a representation of electrode array for impedance sensing, stimulus current and discrete recording of time domain stimulus response using 20 electrodes in the path of flow cells.

Figure 2A:
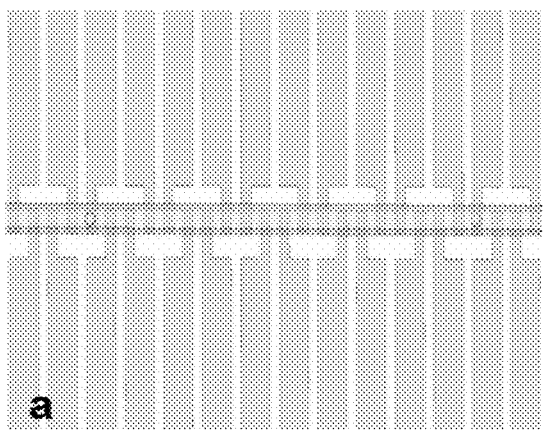
FIG. 2A-2C Schematics of electrodes, channel and OFFSET chip.
Figure 2B:
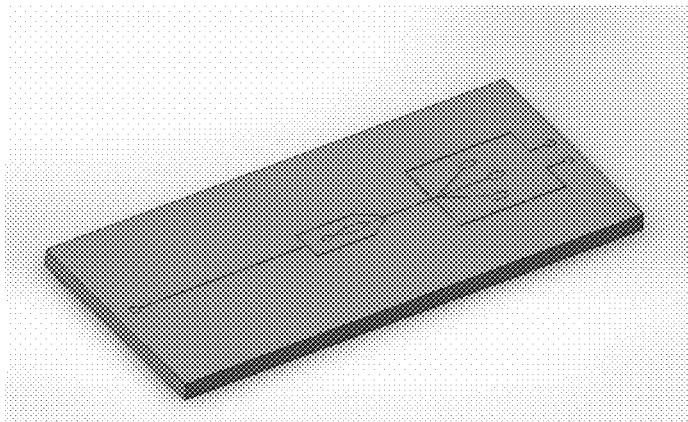
Figure 2C:
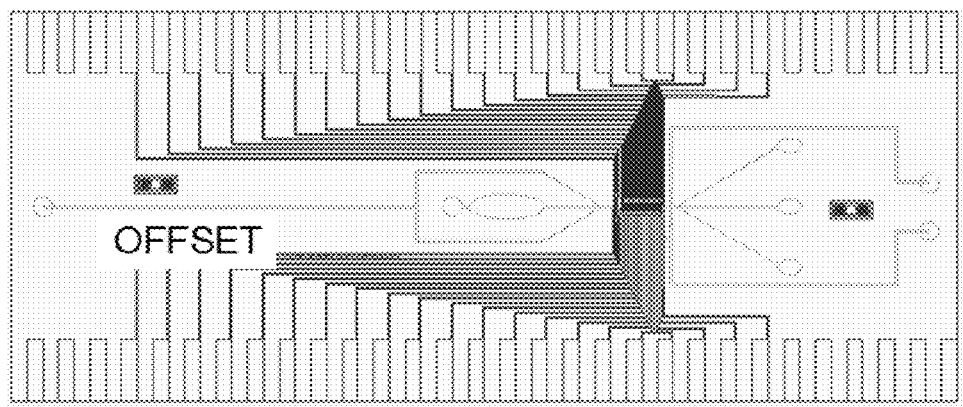
Figure 3:
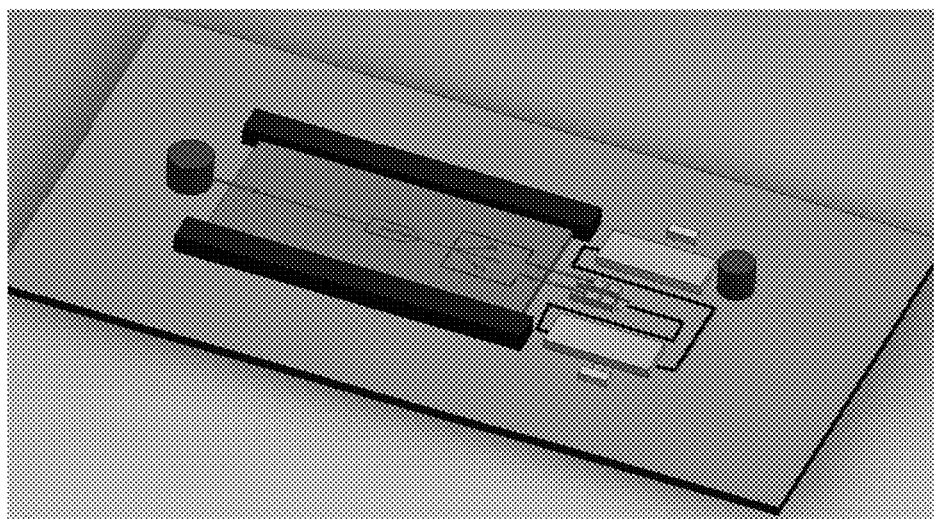
FIG. 3 Schematics of OFFSET Manifold for fluidics and electrical interface.
Figures 4A, 4B, 4C:
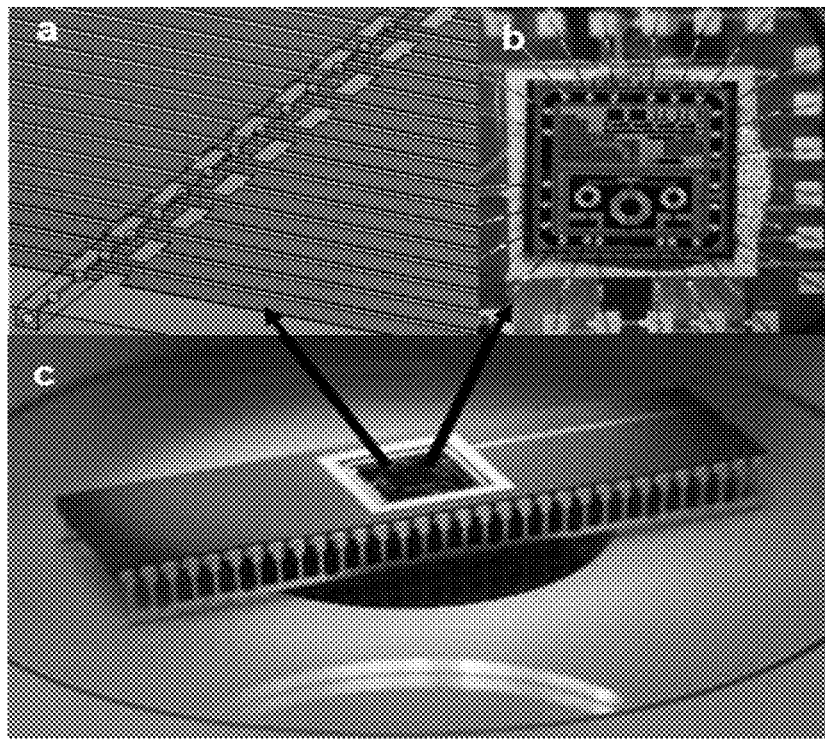
FIG. 4A-4C Electronics Integration. Planar electrodes in the channel, wirebonded multichannel bare die amplifier, electrodes and fluidics package for signal cell detection.

The OFFSET system includes a sheath flow fluidics, single cell impedance detection unit, stimulus current circuit, current response recording circuit, cell sorting fluidics and software control. The sheath flow control is facilitated with syringe pumps and cell sorting fluidics is controlled by a set of valves. The iPS cells are diluted and delivered in to the core flow inlet. The detection of single cells by the differential impedance circuit triggers the stimulus current that last for a few millisecond in the channel electrodes. In the meantime the stimulus response field potential of the flowing cells are recorded by the array of electrodes (described in FIGS. 2A-C) and the field potential signature of the cell is reconstructed from the recorded electrodes. A high impedance low noise multichannel differential amplifier with artifact suppression algorithm for recording the signals is employed. The field potential signatures are compared with the prerecorded response curves from the database and the cell is deflected in to the corresponding outlet channel by the activation of the flow switching valves. Several cell lines such as Fibroblast based iPS cells, cardiac cells, muscle cells is used at a concentration of 2000 cells per uL for sorting. In validation experiments, the electrical recording is compared with parallel fluorescent based Calcein assay detection experiments. The real time fluorescence detection system includes a Tungsten-halogen lamp as an excitation source and a CCD detector. FIG. 3 shows the schematic of OFFSET manifold for fluidics and electrical interface. OFFSET chip, electrical interface cards, pumps, valves, reservoirs for pressurized air and sorting fluid, pressure sensor and fluid refilling port. Electronics Integration is achieved using planar electrodes wirebonded to a multichannel bare die amplifier along with the fluidics package as shown in FIG. 4A-C.

Figure 5:
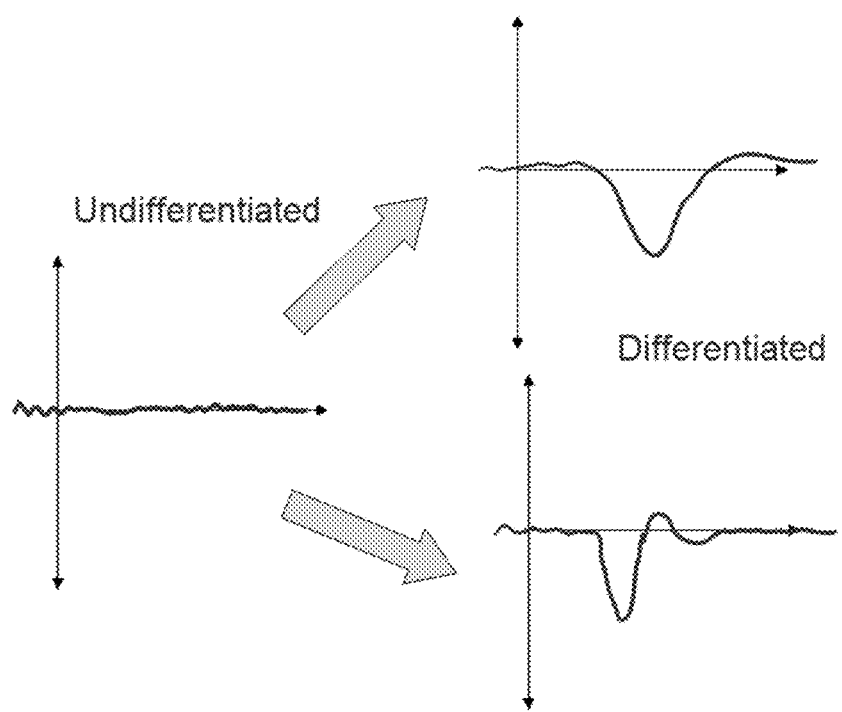
FIG. 5 Field potential based characteristics of undifferentiated and different differentiated species of iPSC.
Figure 6:
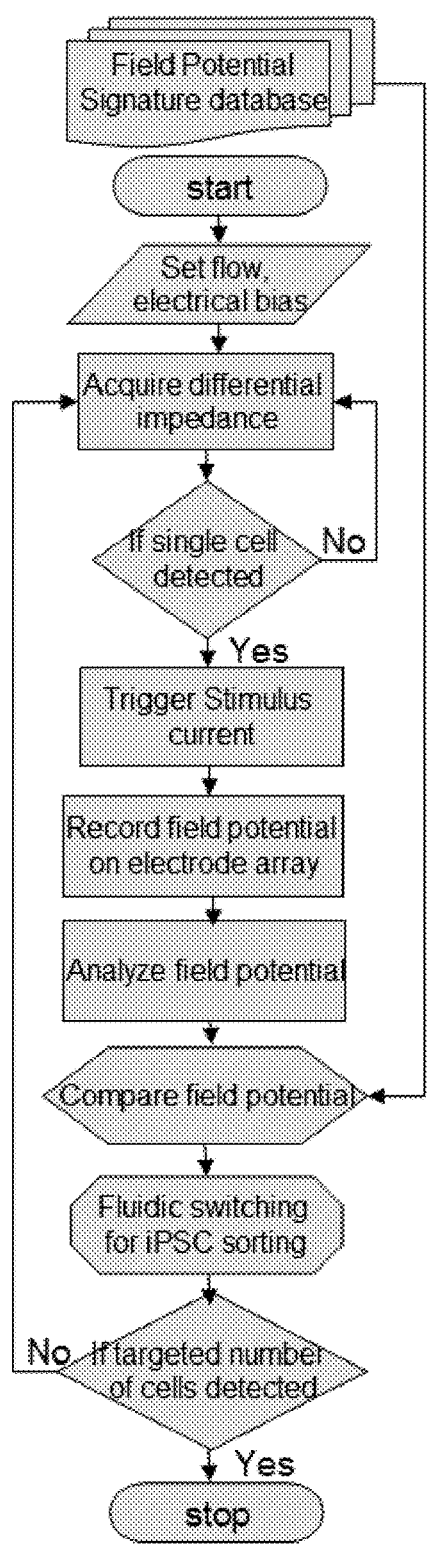
FIG. 6 Flow chart showing the operation of the stem cell sorting system
Figure 7:
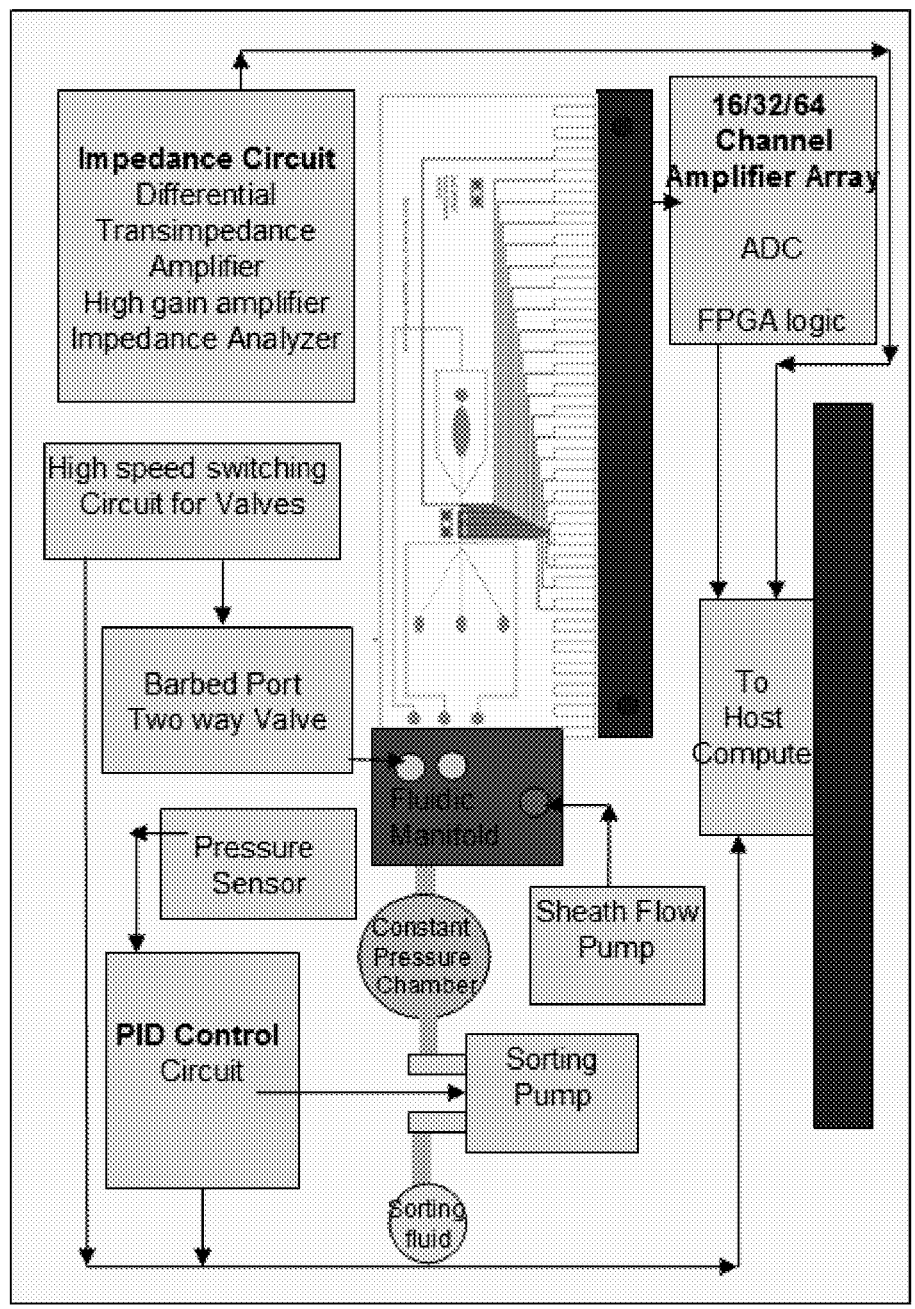
FIG. 7 Complete schematics of OFFSET system.

The OFFSET system is characterized for the sorting efficiency, the purity of the enriched sample, and the differentiated cell throughput. The pluripotency of sorted iPSCs from the OFFSET system is assessed using standard protocol such as gene expression markers, antigen markers, and epigenetic markers. The performance metrics of the integrated OFFSET system such as specificity, purity can be established by cell morphology, quantitative immunochemical and RT PCR assay methods. Validation and verification of electrical signature based sorting is carried out using parallel Calcein fluorescent dye signal recording. The extracellular field potential experiments for different species of neural stem cells, cardiac cells, neurons, glia, muscle cells under static flow conditions is performed in order to compare with the flow based system. Cell sorting is performed after distinguishing between undifferentiated and differentiated stem cells and to achieve a throughput of 100 cells per second using much diluted sample. The integrity of targeted cells is evaluated by comparing the morphology of cells before and after sorting using OFFSET system. The cell product sterility is assessed using standard clinical laboratory techniques. Commercially viable scaled up prototype can be built at 100% specificity with a throughput of 1000 cells per sec for sorting different cell lineages for different clinical iPS cell based therapies. An example of field potential signal for undifferentiated stem cells and differentiated cells is shown in FIG. 5. The reconstructed field potential signal is post-processed by an artifact suppression algorithm to eliminate any artifacts through a combination of template subtraction, linear filtering, and least squares exponential curve fitting. Based on automated analysis of field potential signature, the outlet flow is switched to one of several output reservoirs using external electromechanical valves or additional pressure flow fluidics. FIG. 6 depicts the operation of the OFFSET device and FIG. 7 shows the system integration.

TABLE 3

Cell sorting throughput of OFFSET system

| | |
|---|---|
| Length of sorting fluidics channel | 500 mm |
| Volume of fluid in the channel along with 1 cell for sorting (50 mm × 100 mm × 0.5 mm) | 2.5 nL |
| Number of cells in 1 mL | 400 |
| Velocity of the cells flow | 0.1 m/s |
| Maximum flow rate of cells inlet (50 mm × 100 mm) | 0.5 uL/sec |
| Number of cells sorted per second | 200 |
| Average number of differentiated cells sorted per second (assuming 50% contamination) | 100 |
| Average numbers of differentiated cells targeted to sort per second | 1000 |

Figure 8:
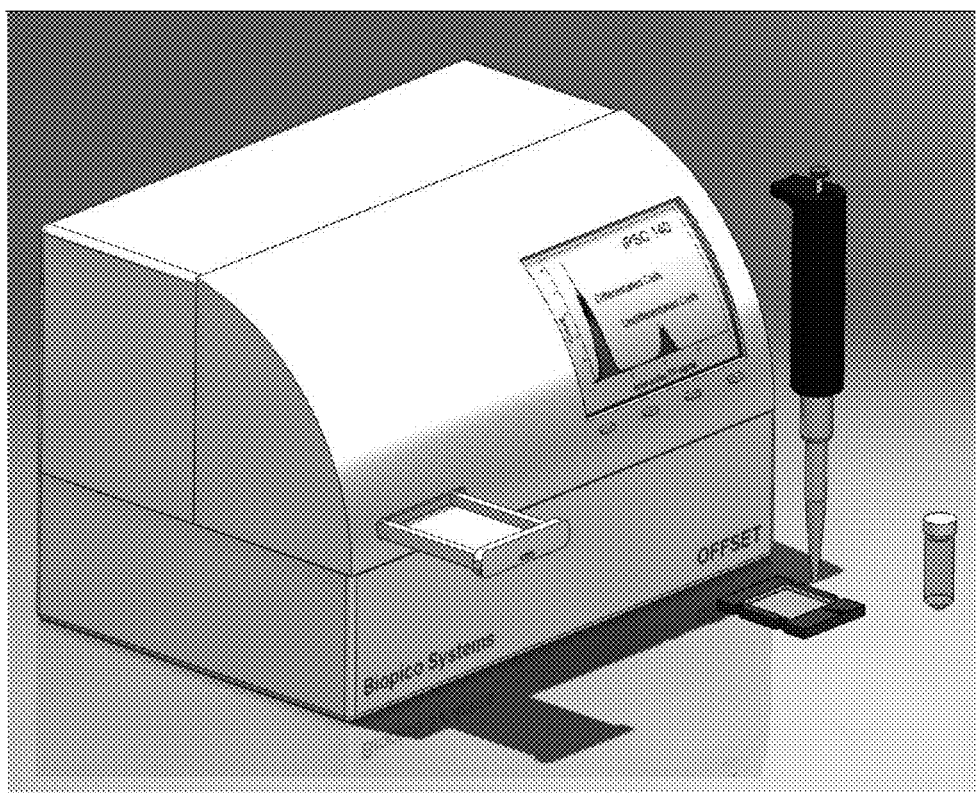
FIG. 8 Prototype OFFSET System.

The parameters such as the sorting efficiency, the purity of the enriched sample, and the differentiated cell throughput are evaluated. The efficiency of the sorting routine measures the ratio of successfully sorted target cells to the total number of target cells detected. The efficiency depends on the sorting cell concentration, the nature of the cells, the flow rate of fluidics, and the electrical signal recording and an efficiency of 95% is expected. The purity, or final cell fraction, of the enriched sample is also dependent on the signal to noise ratio of the electrical FP signatures, rate of cell arrival, switching time duration, and the heterogeneity in the differentiation of the iPSC. It is determined that the optimal lengths of switching for the chips are determined to be 0.5 mm according to the sorting efficiency and sample purity at various sorting durations. The cell sorting throughput is an important aspect of the sorter for potential applications. Conventional FACS systems can achieve rates of 100 k cells/s while microfluidic cell sorters using fluidic switching mechanisms are generally on the order of 10-100 cells/s. The cell sorting throughput of OFFSET system using the flow and cell parameters are calculated to be 100 cells/sec is presented in Table 3. As different therapeutic applications of stem cell therapy would require million to billion number of iPS cells the system can be optimized to a throughput of 1000 cells/sec. FIG. 8 shows the prototype of an OFFSET chip.

Figure 9:
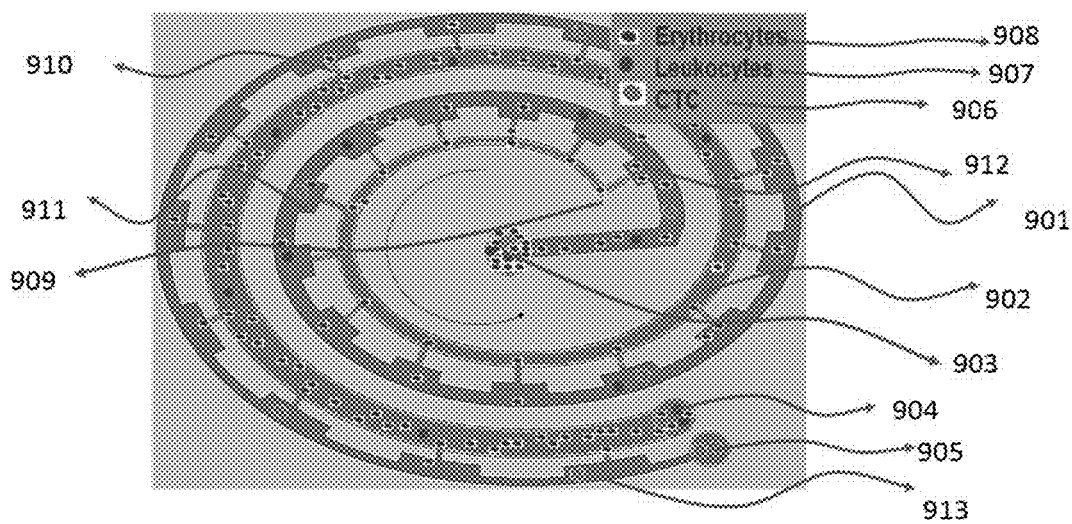
FIG. 9 Geometrical schematics of CTC sorting and diagnostics (f-BIOPSY) chip with width gradient, periodic pinching regions in spiral microfluidic channels.

Flow Driven Blood Based Inexpensive on-Chip High Performance Sorting Using Yoked Channels The CTC sorting and diagnostics (f-BIOPSY) chip includes a spiral microfluidic system having at least two spiral microfluidic channels, an outer spiral microfluidic channel with decreasing width where blood sample is introduced for sorting and an inner spiral microfluidic channel with increasing width where RBC and leukocytes can be extracted. The spiral microfluidic channels are connected with "yoke" channels which allow only smaller particles to move from the outer spiral microfluidic channel to the inner spiral microfluidic channel due to using dean flows and differential migration under inertial microfluidics (FIG. 9). The spiral microfluidic system also includes periodic pinching regions of decreasing width (100-20 μm) in high aspect ratio 9-loop spiral microfluidic channel with a height of 100 μm to sort erythrocytes from leukocytes and to sort CTC from leukocytes in a convenient single step.

Figure 10:
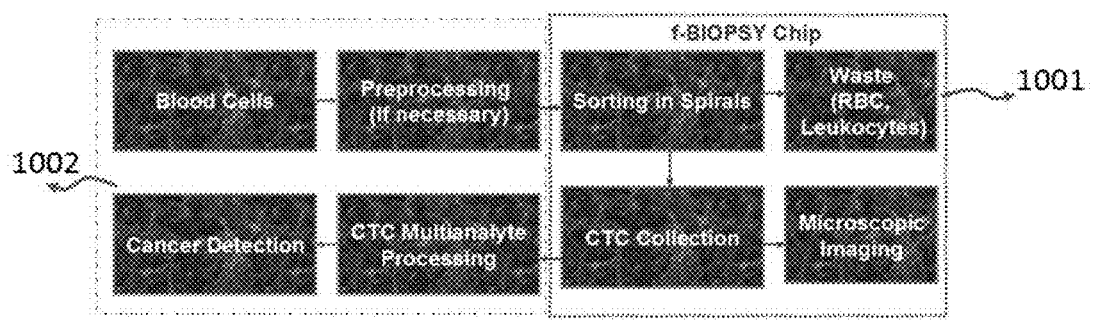
FIG. 10 CTC sorting and diagnostics System for cancer diagnostics.

The f-BIOPSY system includes a preprocessing step for blood, a sorting step in f-BIOPSY chip and CTC processing for cancer diagnostics. The f-BIOPSY system as shown in FIG. 10 takes whole blood diluted to 1%-10% hematocrit sample to efficiently sort CTC. The sorted CTC cells are observed at the collection chamber using a microscope and imaged using immuno-fluorescence assays. The CTCs are collected and processing for multianalyte protein expression profiling. The f-BIOPSY system can be integrated with flow devices to power the inertial fluidics for sorting, microscopic imaging, PCR thermal cycler, and control & analysis software for cancer diagnostics.

The characterization and evaluation processes involve f-BIOPSY chip performance and f-BIOPSY system performance. The high-throughput f-BIOPSY chip can be evaluated for each step of processes for the optimization of geometry parameters and characterizing the optimized device for performance metrics by analyzing the specificity, accuracy of the sorted cells. CTC recovery rate and the efficiency of the device with hematocrit percentage are measured. Our goal is to achieve greater than 95% specificity and accuracy. This success can open up possibilities for faster-than-ever, low cost, high-throughput more efficient and more sensitive devices for multi-analyte improved cancer early detection, diagnosis, prognosis and treatment monitoring.

As illustrated in FIG. 9, a spiral microfluidic channel system includes primary spiral microfluidic channel 901 coupled to inlet 903, and secondary spiral microfluidic channel 902 coupled to primary spiral microfluidic channel 901. As illustrated in FIG. 9, primary spiral microfluidic channel 901 includes pinching regions 911, where secondary spiral microfluidic channel 902 is connected to pinching regions 911 of primary spiral microfluidic channel 901 through interconnect channels 910. Primary spiral microfluidic channel 901 and secondary spiral microfluidic channel 902 are substantially concentric. As illustrated in FIG. 9, primary spiral microfluidic channel 901 has a decreasing width from inlet 903 to outlet 905, while secondary spiral microfluidic channel 902 has an increasing width from channel inlet 909 to outlet 904.

As illustrated in FIG. 9, the spiral microfluidic channel system is configured to separate cells, such as CTCs 906, leukocytes 907 and erythrocytes (RBCs) 908, for example. Cells, for example, in a blood sample are delivered at inlet 903, and flowed through primary spiral microfluidic channel 901 and secondary spiral microfluidic channel 902, and collected at outlet 905 of primary spiral microfluidic channel 901 and outlet 904 of secondary spiral microfluidic channel 902. As illustrated in FIG. 9, CTCs 906 are separated from other cells such as leukocytes 907 and erythrocytes (RBCs) 908 through primary spiral microfluidic channel 901 and collected at outlet 905, while leukocytes 907 and erythrocytes (RBCs) 908 are collected at outlet 904 of secondary spiral microfluidic channel 902.

The width of each interconnect channels 910 between two successive spiral microfluidic channels depends upon the size of the cells or particles or species under sorting. The length of each periodic pinching regions 911 depends on the flow rate of the microfluidics. The lengths of the pinching regions can increase from the centermost pinch region 912 to the outermost pinch region 913. In one implementation, pinching regions 911 can be periodically disposed along a concave sidewall of primary spiral microfluidic channel 901. In another implementation, pinching regions 911 can be periodically disposed along a convex sidewall of primary spiral microfluidic channel 901.

Figure 11A:
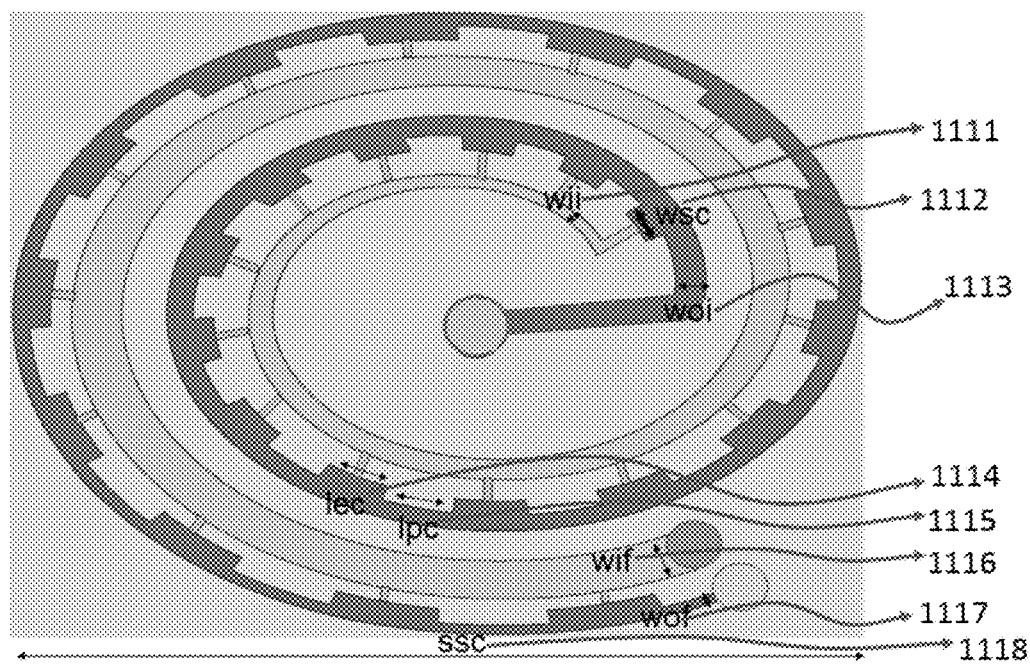
FIG. 11A-11B Optimization parameters of f-BIOPSY Chip. 3-D geometry of the portion of the f-BIOPSY chip.
Figure 11B:
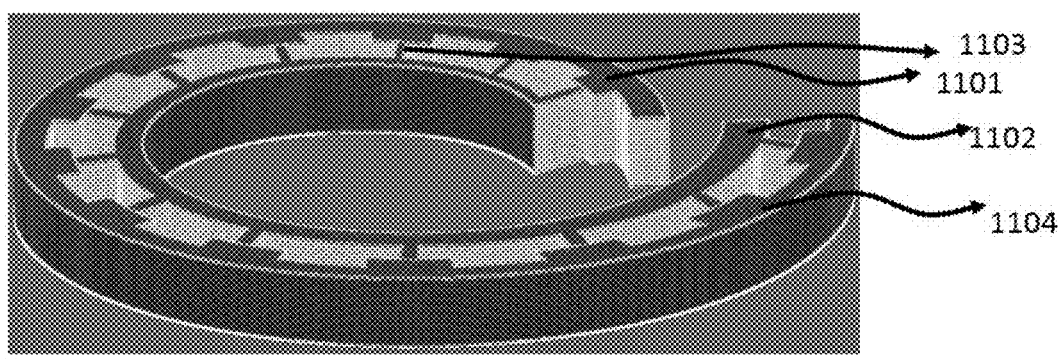

FIG. 11A-B shows a 3-dimensional structure of a portion of a chip having a spiral microfluidic channel system. The primary spiral microfluidic channel 1101, secondary spiral microfluidic channel 1102, interconnect channels 1103 and pinching regions 1104 are shown. The initial geometry can comprise a 9-loop (100 μm to 20 μm)×100 μm (W×H) double spiral channel with two separate outlets. The number of turns and the width gradient are optimized for the high specificity of sorting. The decreasing width gradient periodic pinching regions can provide high efficiency. In order to achieve high specificity in the sorting of CTCs from whole blood the spiral widths (wii 1111, woi 1113, wif 1116, wof 1117—widths of inner and outer spiral at the initial and final positions) are adjusted. Further the length of the expanded and pinched channels (lec 1114, lpc 1115) are also adjusted to increase the efficiency of the sorting of CTCs. The 'pinching' width is a key feature of the f-BIOPSY chip for the successful isolation of CTCs from blood. The contraction width along this pinching region is fabricated to be comparable (smaller) to the CTC diameter, ensuring that the cells are effectively 'squeezed' as they traverse through the contraction channels. The number of turns of the spiral channels (ssc 1118—size of spiral channels) is also optimized for the high efficiency and specificity of the sorted cells. The widths of side channel (wsc 1112) are adjusted to avoid any leakage of CTC in to the RBC waste channel. To study the effect of aspect ratio, microchannels of height 75 mm, 100 um and 150 um can be fabricated yielding aspect ratios of 3.75, 5 and 7.5, respectively. The high aspect ratio microchannels preferentially equilibrate cells along the longer channel dimension and process the sample at higher flow rate, thereby increasing the throughput.

Figure 12A:
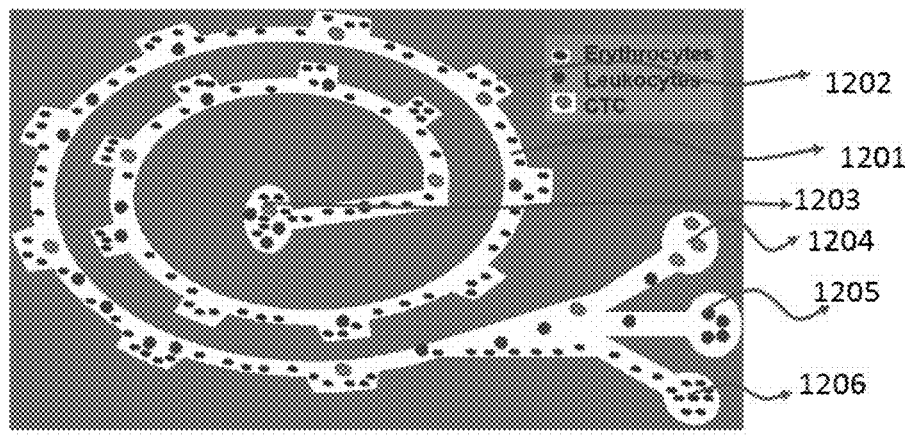
FIG. 12A-12B CTC enrichment using decreasing width gradient periodic pinching regions in spiral channel inertial fluidics. Modified f-BIOPSY chip to isolate all CTCs of overlapping sizes using multistep sorting of blood.

The operation of a f-BIOPSY chip is based on the phenomenon of inertial microfluidics in spiral microfluidic channel 1201 having pinching regions 1202 in convex configuration 1202, where pinching regions 1202 are disposed on a convex sidewall of spiral microfluidic channel 1201. As illustrated in FIG. 12A, a blood sample having CTCs, leukocytes and RBCs is delivered at inlet 1203, and separated at outlets 1204, 1205, 1206, respectively. In f-BIOPSY microchannels, under the Poiseuille flow condition, particles of varying sizes equilibrate at distinct positions along the microchannel cross-section under the influence of inertial lift and Dean drag forces. The high aspect ratio microchannel using shear modulated inertial lift forces that efficiently equilibrates all the cells along the channel side walls. The CTCs can be isolated from whole blood in periodic pinching regions of outer spiral channels. As the cells flow in the spiral channel the bigger or heavier cells undergo higher inertia and do not undergo deviation in their paths where as small cells undergo deviation towards the expanding region. The erythrocytes from blood can move towards expansion and are extracted in to the inner spiral channel. The larger CTCs (RBCs ~5 μm; leukocytes ~8-14 μm; CTCs ~16-20 μm diameter) are collected at the outer outlet with 90-100% recovery. Due to size proximity of leukocytes, CTCs collected may contaminate with leukocytes. The decreasing width of the outer spiral channel helps in the improved specificity of the sorting of CTCs. As illustrated in FIG. 10, a f-BIOPSY system may include f-BIOPSY chip 1001 for on-chip processing of cells and off chip 1002 for off-chip pre-processing of the cells for cancer diagnosis from whole blood.

In order to operate the f-BIOPSY System, whole blood can be filtered for any clusters and diluted to adjust the hematocrit before introducing into the f-BIOPSY chip. The sorted CTCs can be collected for multianalyte gene expression profiling based cancer diagnosis.

Figure 12B:
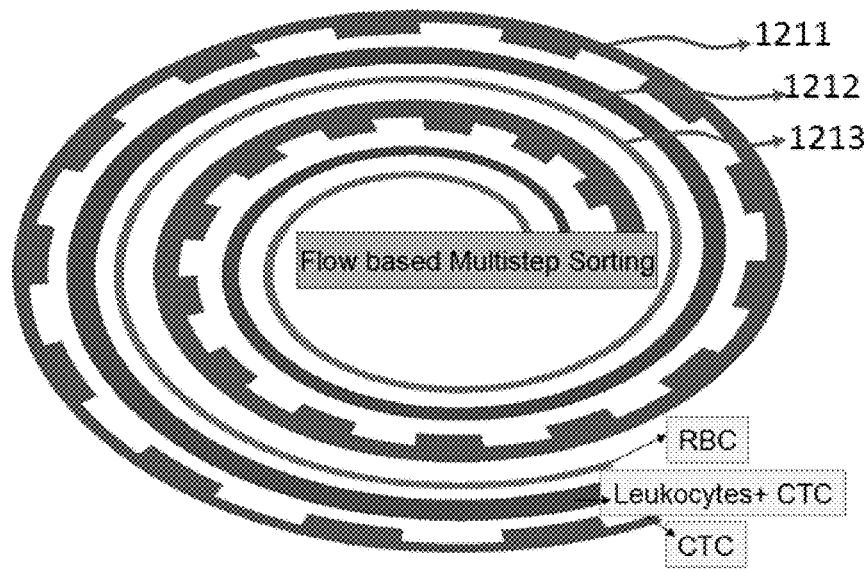

As with any size-based CTC separation technique, a major limitation of this device is its inability to isolate CTCs that overlap the peripheral blood leukocyte size scale. In such case, the f-BIOPSY chip can be upgraded with an additional spiral channels (Triple Spiral shown in FIG. 12B) for separating RBCs, leukocytes and CTCs using spiral microfluidic channels 1211, 1212, and 1213, respectively. It is noted that although one or more interconnect channels are not explicitly shown in FIG. 12B, it should understood that spiral microfluidic channels 1211, 1212, and 1213 may be respectively connected through interconnect channels.

The CTCs of larger sizes can be collected and used for experimenting gene expression profiling and further cell culture. The CTCs of smaller sizes can be collected along with the leukocytes and can be sorted out using immuno-magnetic assays for genomic PCR or immunoprotein analysis. Although sample dilution is required in the f-BIOPSY system, the chip runs at high flow rate and the chip allows for easy parallelization with the ability to analyze milliliters of clinical blood samples within minutes.

Figure 13:
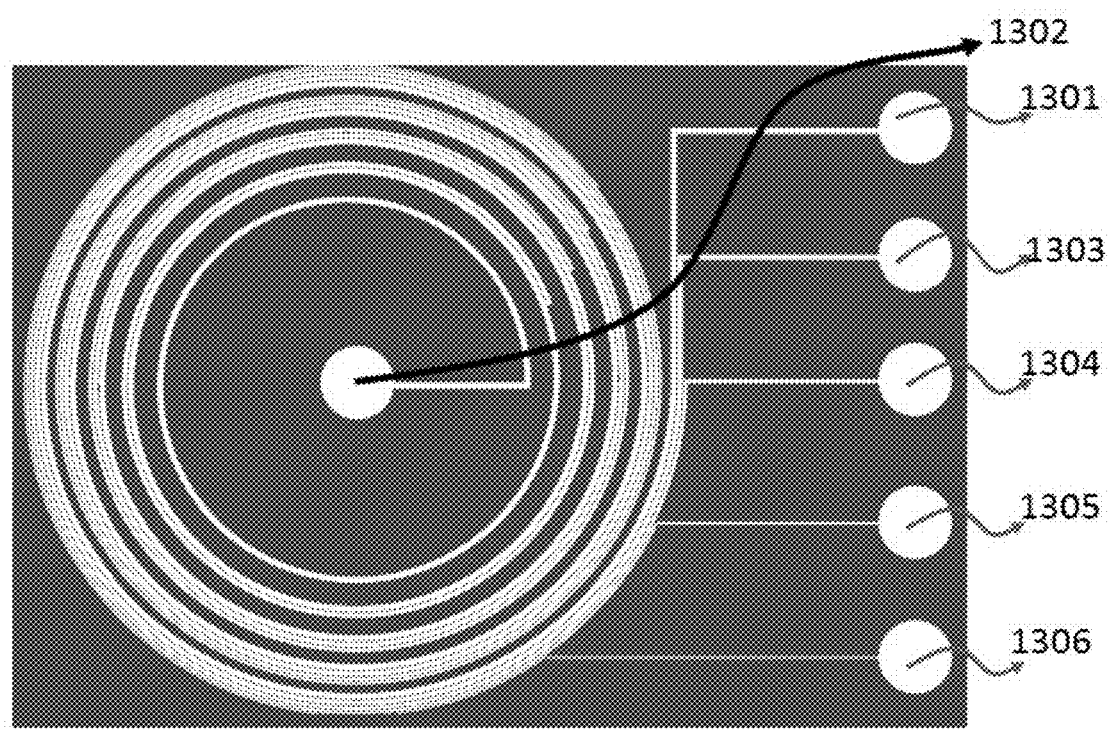
FIG. 13 Digital Centrifuge: Multiple size particulate sorting with 5 spirals.
Figures 14A, 14B, 14C, 14D, 14E:
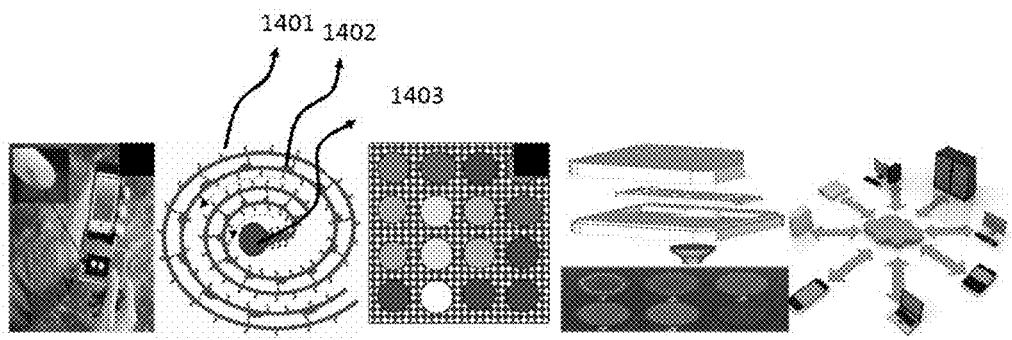
FIG. 14A-14E Schematic diagram of a serum based mobile driven rapid test (SMART) system. The system takes blood sample at the inlet of SMART chip from finger tip and docks at the cell phone. Serum from blood is separated using a spiral channel actuated by acoustic cavitations streaming pump. Serum reacts with the reagents for colorimetric assay. Imaging is carried out using a transmission mode lensless optical setup lit by an LED. Smart phone performs computation of health data and transmit to a cloud computing server.

A generalized the size based sorting technique in to a digital centrifuge by incorporating parallel multiple spiral based microfluidic sorting channels 1301, 1303, 1304, 1305 and 1306, using a single inlet 1302 similar to traditional centrifuge system with the additional provision of low cost, automatic and robust platform is shown in FIG. 13. It is noted that although one or more interconnect channels are not explicitly shown in FIG. 13, it should understood that channels 1301, 1303, 1304, 1305 and 1306 may be respectively connected through interconnect channels.

Serum Based Mobile Driven Analyzer for Rapid Tests

In the project on 'Serum based Mobile driven Analyzer for Rapid Tests (SMART)' shown in FIG. 14A-E, a SMART chip and system for Smart Phone Driven Blood-Based Diagnostics is developed. In this system, personal diagnostics information from whole blood is derived using a microfluidic chip and transmitted to cloud computing network for access to relevant users. A serum separation chip using spiral fluidics actuated by acoustic cavitation streaming can be developed for calorimetric assays. The SMART chip can be integrated with mechanical, electronic, optical components for carrying out POC diagnostics powered by cloud computing. Biochemical techniques can be carried out off the chip to develop and optimize colorimetric bioassay. Fluidic, electronic, optical and bioassay experiments can be performed on the chip independently and collaboratively in order to evaluate the chip and system.

Figure 15A:
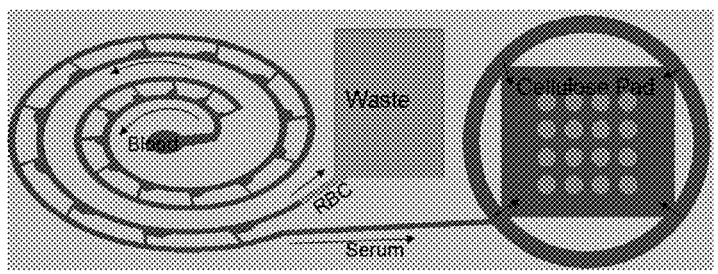
FIG. 15A-15B Schematic diagram of a SMART chip for serum separation from whole blood and colorimetric assay. Serum separation spiral microfluidic channel is actuated by acoustic cavitations streaming pump.
Figure 15B:
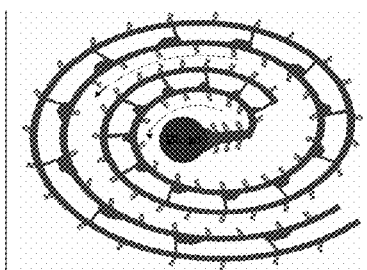
Figure 16:
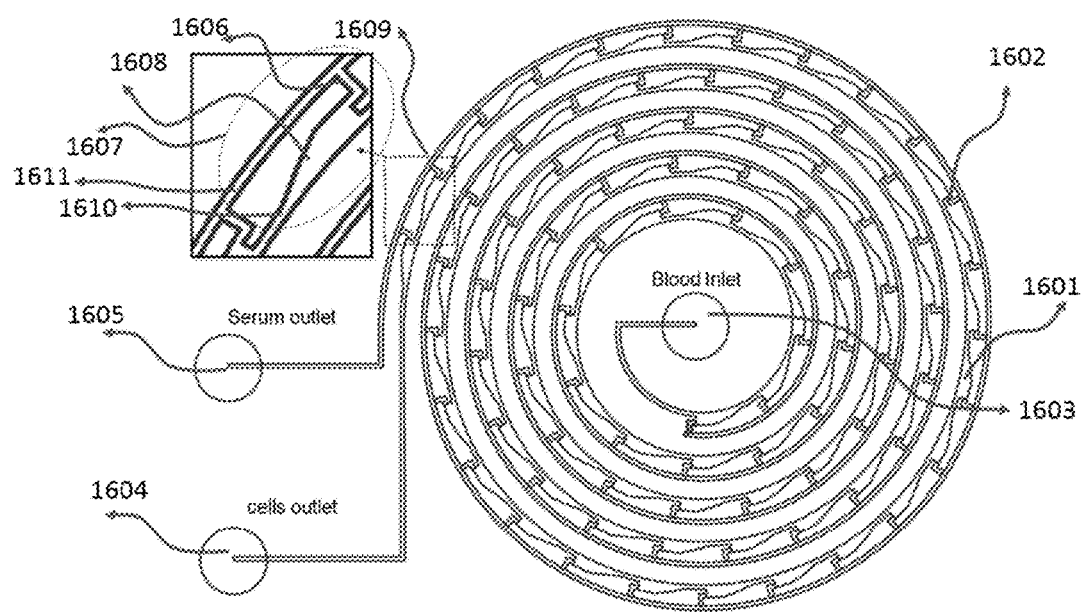
FIG. 16 Schematics of serum separation from whole blood using double spiral microfluidic channel.

A compact disposable SMART chip can be developed to sort serum from blood and to perform colorimetric assay on nitrocellulose pads. The rapid serum separation from whole blood is accomplished using cascaded serum extraction regions in spiral microfluidics (FIG. 15A). The separated serum enters multiple sides of cellulose nitrate pads for carrying out colorimetric assays for diagnostics. In order to actuate the pumping along the channels an acoustic cavitation streaming pump can be utilized (FIG. 15B). This provides not only rapid assay but also enables low power operations. The serum extraction is carried out from whole blood inlet 1603 to serum outlet 1605 and cells outlet 1604 using passive microfluidics with faster protocol and undiluted blood using the technique shown in FIG. 16. The optimized geometry of the device with interconnect channel 1602 can provide efficient separation with out clogging or sample dilution and extraction of plasma from whole human blood. In this chip, the cell-free layer is considerably enhanced locally by geometric singularities such as an abrupt enlargement of the channel 1601 or a cavity along the channel. The extraction yield, the extraction purity, the flow rate stability regime and the range of sample dilutions are optimized. In straight microchannels, neutrally buoyant particles experience lateral migration in a circular Poiseuille flow, resulting from two competing inertial Effects: one due to the interaction with the wall, which produces a lift force away from the wall, and the other due to the shear and curvature of the Poiseuille velocity profile, which induces migration. A magnified image of a portion of the SMART chip 1609 is shown. In the SMART chip multiple units of extraction channel 1607 are arranged in a spiral fluidics for rapid and efficient extraction of serum. Whole blood entering primary spiral microfluidic channel 1610, pinching region 1608 and serum is extracted through the "L" shaped interconnect channel 1606 to secondary spiral microfluidic channel 1611.

Figure 17:
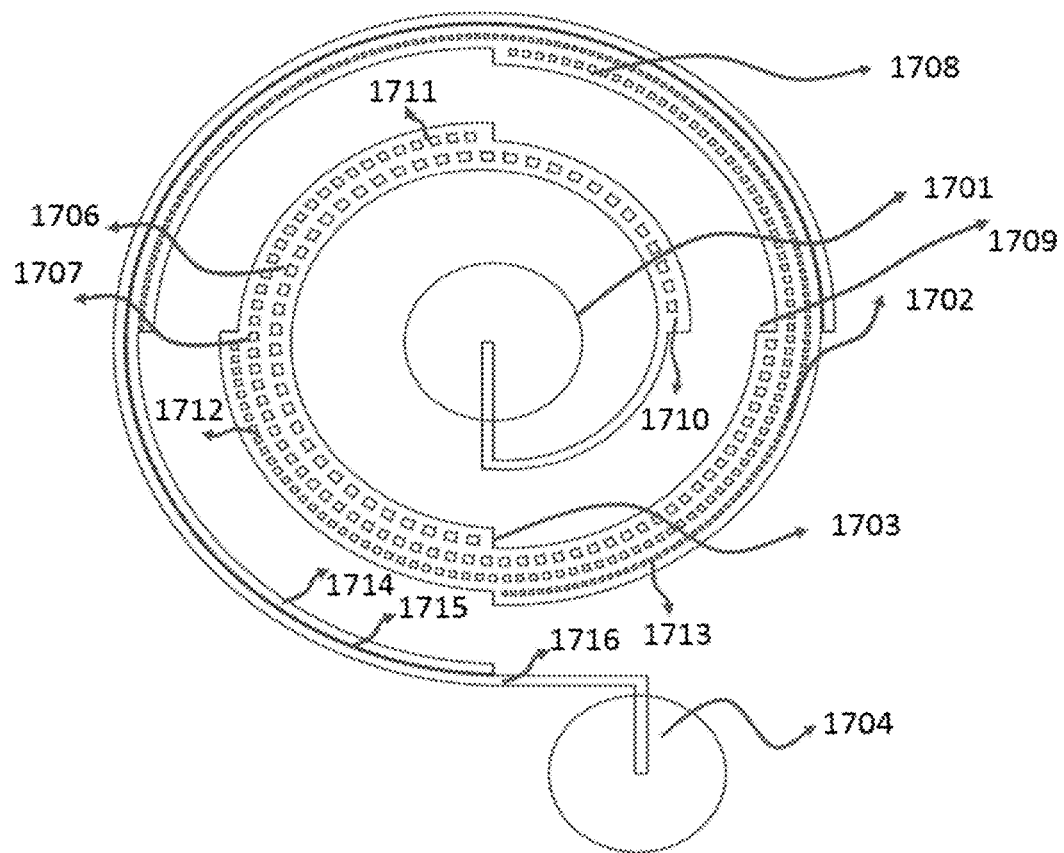
FIG. 17 Schematics of serum separation from whole blood using filters in spiral microfluidic channel.

FIG. 17 shows an alternative schematic for serum separation at output 1704 from a whole blood from inlet 1701 using successive cell filtering. In this chip, several layers of spiral microfluidic channels with decreasing width interconnect channels are shown. As illustrated in FIG. 17, a spiral microfluidic system includes inlet 1701, primary spiral microfluidic channel 1710 and a set of secondary spiral microfluidic channels (e.g., spiral microfluidic channels 1711, 1712, 1713, 1714 and 1716), one or more groups of interconnect channels (e.g., interconnect channels 1706, 1707, 1708 and 1702). The size of the interconnect channels can filter smaller and smaller particles as the blood flows into adjacent spiral microfluidic channels. For example, the width of a first group of interconnect channels 1706 connecting primary spiral microfluidic channel 1710 and secondary spiral microfluidic channel 1711 is 10 um. The width of a second group of interconnect channels 1707 connecting secondary spiral microfluidic channel 1711 and third spiral microfluidic channel 1712 is 5 um. The width of a third group of interconnect channels 1708 connecting third spiral microfluidic channel 1712 and fourth spiral microfluidic channel 1713 is 3 um. The width of a fourth group of interconnect channels 1702 connecting fourth spiral microfluidic channel 1713 and fifth spiral microfluidic channel 1714 is 1.2 um. These spiral microfluidic channels with fractional turns can be seen as several primary or secondary spiral microfluidic channels with ends having no outlet (e.g., ends 1703 and 1709) except outlet 1704 of sixth spiral microfluidic channel 1716 connected to fifth spiral microfluidic channel 1714 through fifth group of interconnect channels 1715. Serum is extracted in the last spiral and collected at the outlet 1704.

Figure 18:
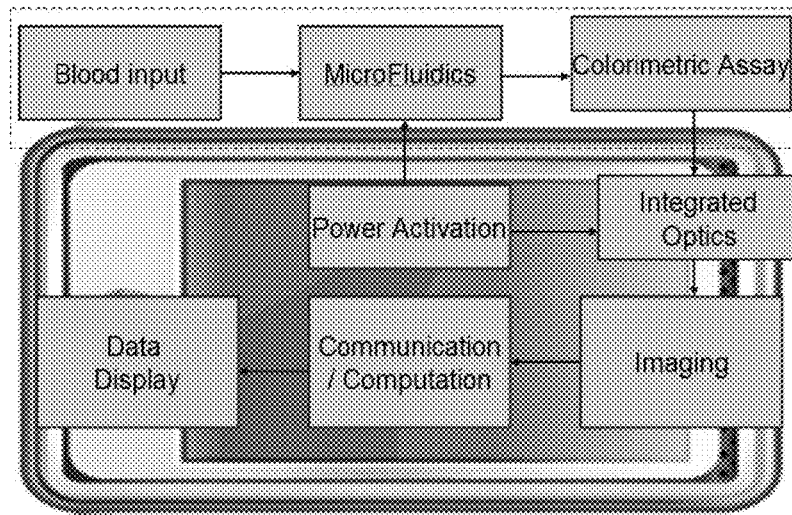
FIG. 18 Schematic diagram of a SMART system hardware for personal diagnostics.

The SMART system (described in FIG. 18) includes a microfluidic compact chip for serum separation from blood and colorimetric assay, a lensless imaging for the quantification of personal diagnostics and a smart phone. The role of smart phone is two fold: 1. to provide electrical power to fluidic, electronic and optical components of the SMART system 2. to provide software control for acquisition, computation, communication and display of diagnostics data for the SMART system. The disposable compact chip performs the colorimetric assay for diagnosing blood. A lensless contact imaging approach is employed to obtain a compact imaging of the colorimetric assay with adequate resolution. The imaging system composed of a housing for reaction chip positioning and light shielding, which can dock a transparent microfluidics-based reaction chip to image through a fiber optic taper. A chip holder with cover assured reproducible positioning of the chip during the measurement and provides shielding from ambient light. Enzyme activities can be measured on cellulose pads inside the microfluidic chip. The camera can be controlled by the smart phone, by means of which light emission intensity and 2D distribution data can be easily acquired and processed. As a proof of concept, the suitability of the device for diagnostics can be demonstrated by performing models of the most common clinical chemistry enzyme activity glucose assay.

Figure 19:
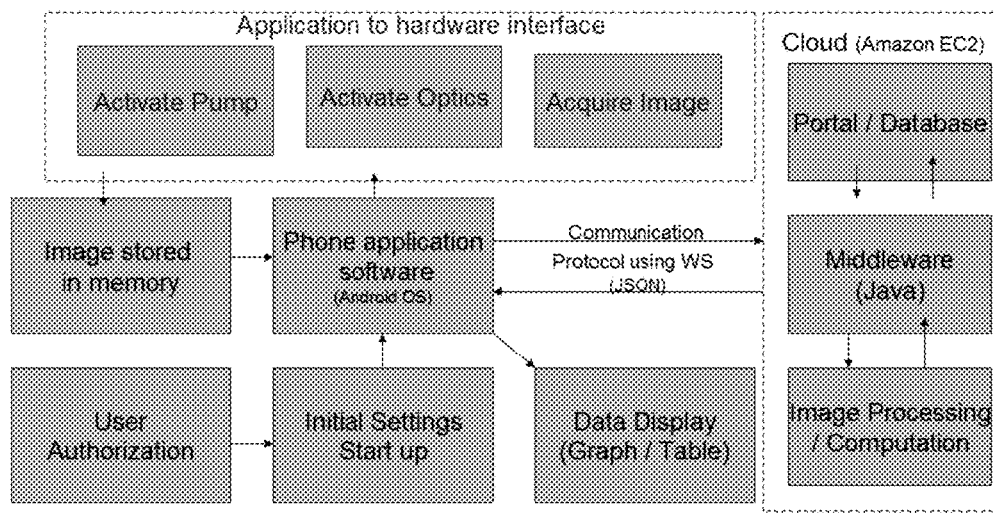
FIG. 19 Schematics of a smart phone for software control, communication, computation and display.
Figures 20A, 20B, 20C, 20D, 20E:
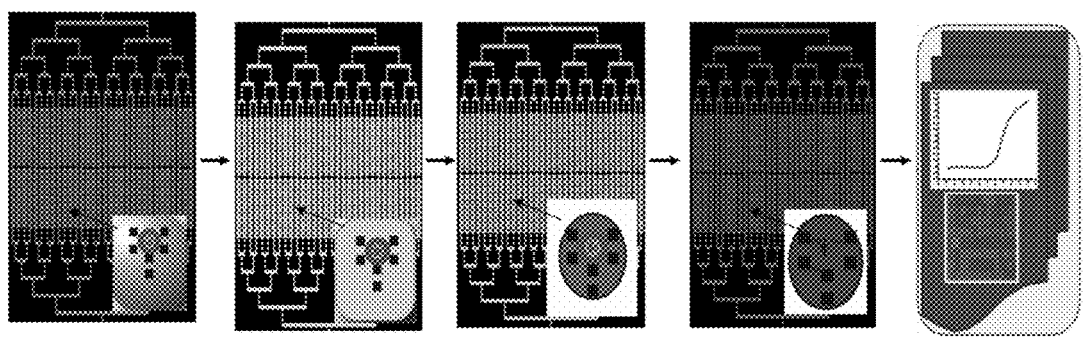
FIG. 20A-20E Schematic diagram of a PILLAR chip/system that can trap and encapsulate thousands of single cells in configured micropillars and perform RT PCR. The operational steps are trap single cells, supply PCR mix and lysis buffer to trapped cells, encapsulate of single cells using immiscible fluidics, thermal cycle by flowing oil from hot/cold baths with synchronized imaging for gene expression profiling and Data processing and Statistical analysis for regenerative medicine or clinical diagnostics.

The smart phone application software as described in FIG. 19, is a central software control of the SMART system. The application software interfaces to the hardware and provide communications to cloud network and user for the display of diagnostic information. A Samsung Galaxy Android phone and communicate to Amazon EC2 cloud computing using JSON communication protocol is used. If the computational power is not sufficient for performing several image processing algorithms at smart phone, the heavy computation is performed at the cloud server. Otherwise smart phone's computing power is used to process the images. The smart phone application software communicates with the Java middleware in the cloud and perform several image processing and computation to extract the diagnostics data. Further the smart phone application software collects the diagnostics data and display at the smart phone for monitoring or to alert the user or patient. GUI or user authorization software at the smart phone end as well as cloud portal is developed. The patients' health information is made available on the cloud network for physicians or health care provides.

Parallel Incubators with Loaded Single Cells for Lysis and Amplification Reactions The single cells or molecules encapsulated picoreactors chip/system as shown in FIG. 20A-E for gene amplified enumeration and/or followed by electrophoresis is critical to the development of pathology, oncogenesis, and other processes of a desired target cell or molecules. The system combines single cell trapping in micropillars, immiscible microfluidics, and fluorescent reverse transcription (RT)-PCR technologies performing molecular diagnostics in a quick, high-throughput, and cost-effective fashion. This highly integrated platform is configured to:

precisely trap a single cell in array of configured micropillars encapsulation of single cells as picoliter reactors using immiscible microfluidics simultaneously perform thousands of single-cell PCR in picoliter volumes rapidly analyze the PCR results on a chip analyze single-cell of large populations for clinical diagnostics or biomedical research The combination of high-fidelity manipulation of single cells and the ability to perform nucleic acid amplification offers the possibility of developing powerful automated instruments.

Figure 21:
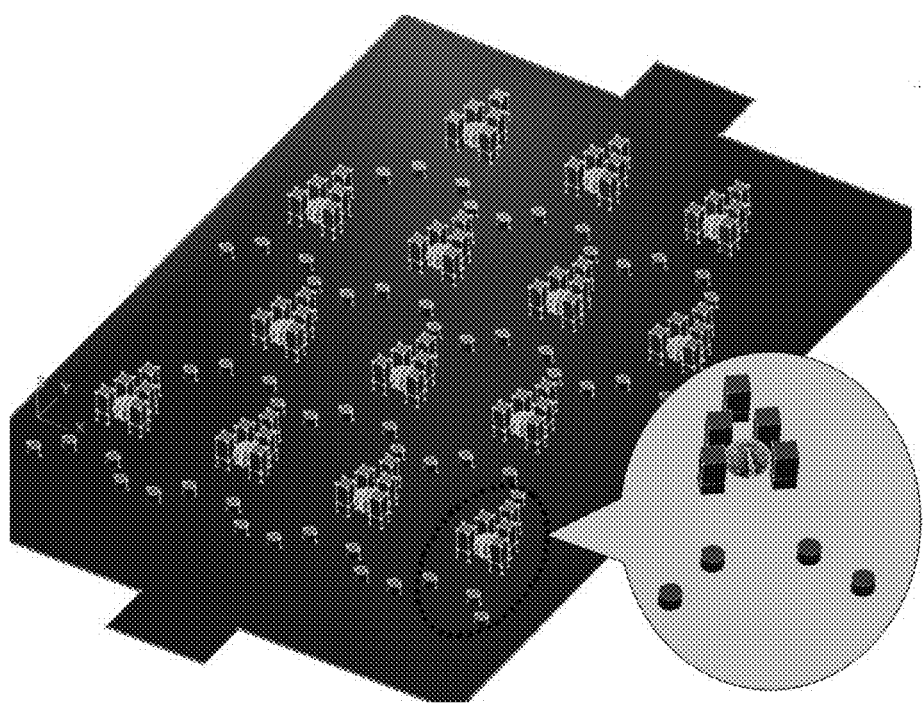
FIG. 21 Aqueous flow showing cells trapped at the micropillar trapping sites in a compartment of the parallel incubators single PCR (PILLAR) chip.

The trapping site configuration with another set of shorter cylindrical micropillars as guide posts (shown in FIG. 21) in front of the trapping site locations by understanding the flow dynamics of the cells is modified. Therefore efficiency of single cell trapping and reactor encapsulation can be much improved to trap single cells for a high throughput of 10 k-100 k range. During encapsulation process, these shorter guiding posts can be immersed in to the oil phase.

Figure 22:
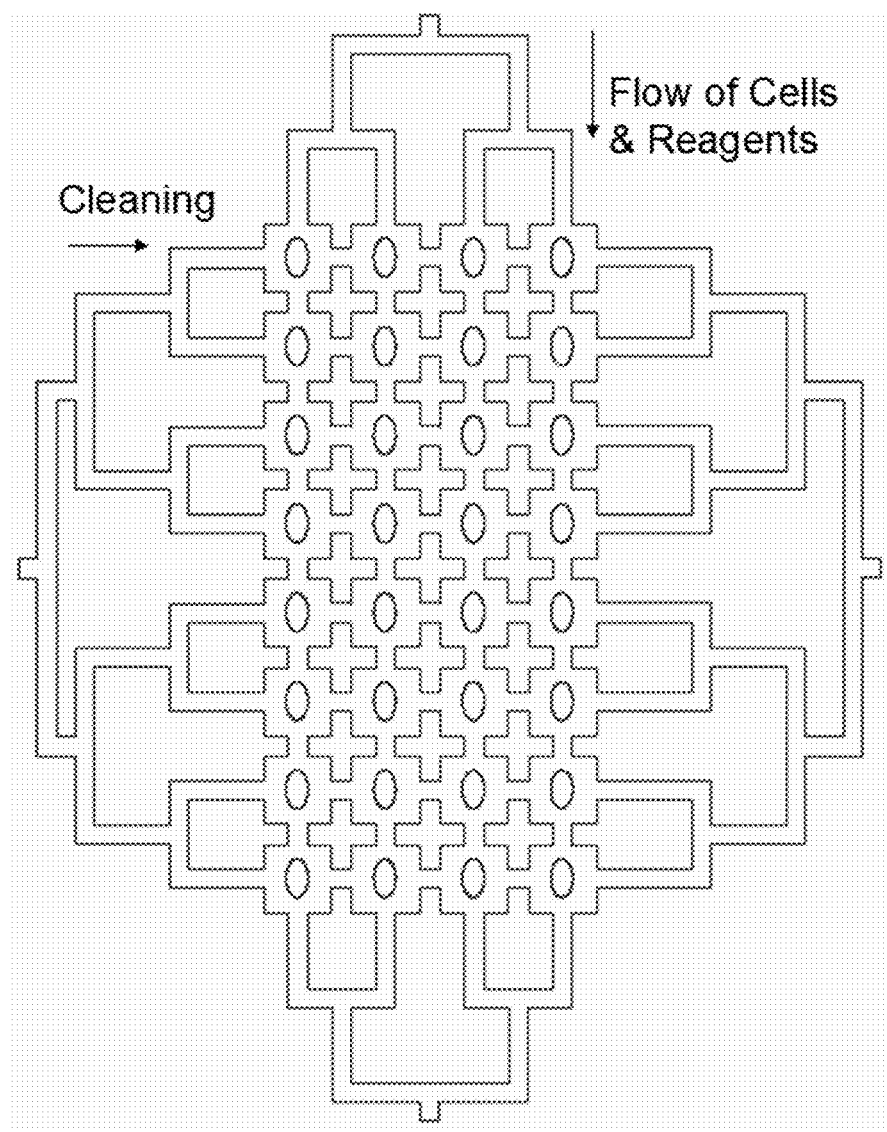
FIG. 22 Fluidics diagram of the massively parallel picoreactor chip with cells and reagents are flowed from the top inlet. Extra cells or cell clusters adhered weakly near the trap sites are cleaned by the flow at the side inlet.
Figure 23A:
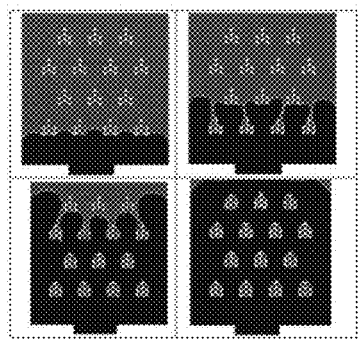
FIG. 23A-23E Successive frames of the formation of encapsulated reactors. Successive frames of thermal convection profile from a temperature of 27° C. to 92° C. in 20 ms. Velocity of flow profile inside the chip with the application of a flow rate with a speed of 0.1 m/s. Kinetics of temperature profile during the convective diffusion of oil from a temperature of 27° C. to 92° C. (for PCR thermal cycling).
Figure 23B:
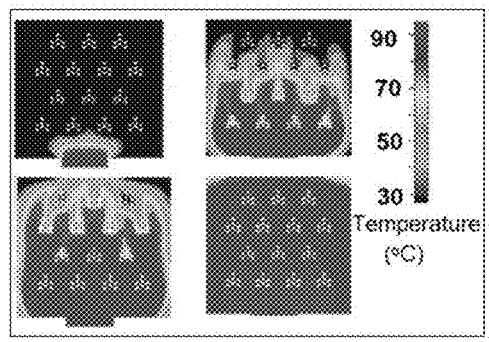
Figure 23C:
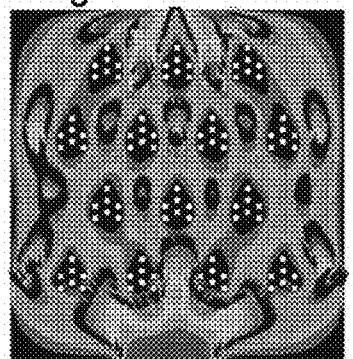
Figure 23D:
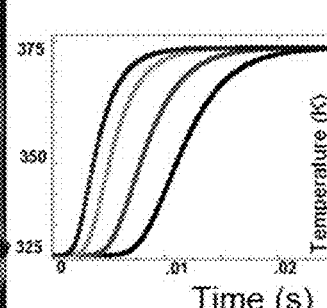
Figure 23E:
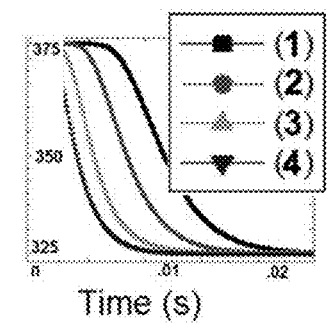
Figures 24A, 24B:
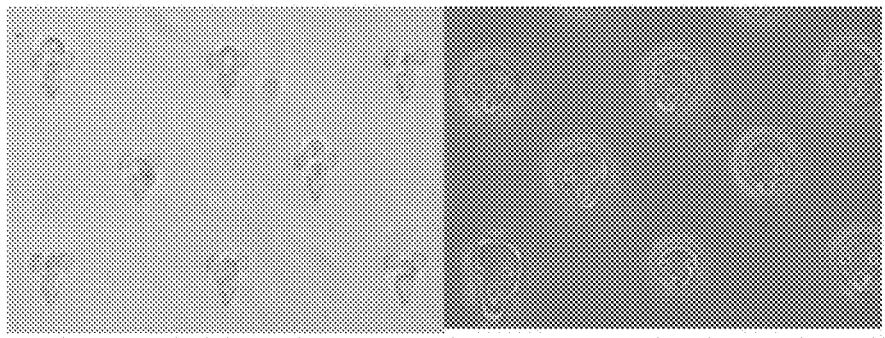
FIG. 24A-24B single cells trapping at a flow of cells at 1 uL/min, encapsulation of aqueous fluid using immiscible fluid at a flow of 5 uL/min.
Figure 25:
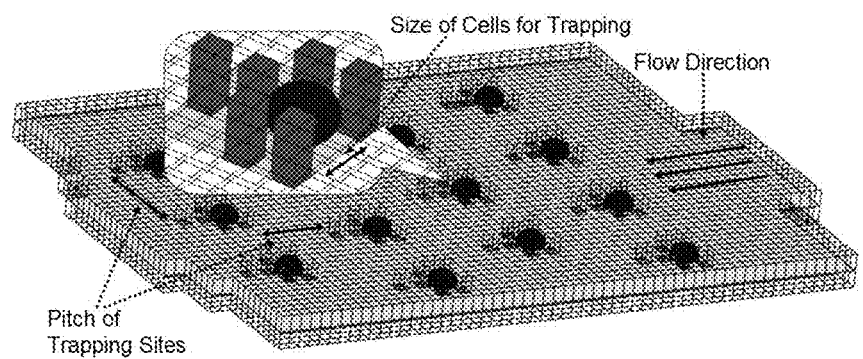
FIG. 25 Aqueous flow showing cells trapped at the micropillar trapping sites in a compartment of the PILLAR chip.
Figure 26:
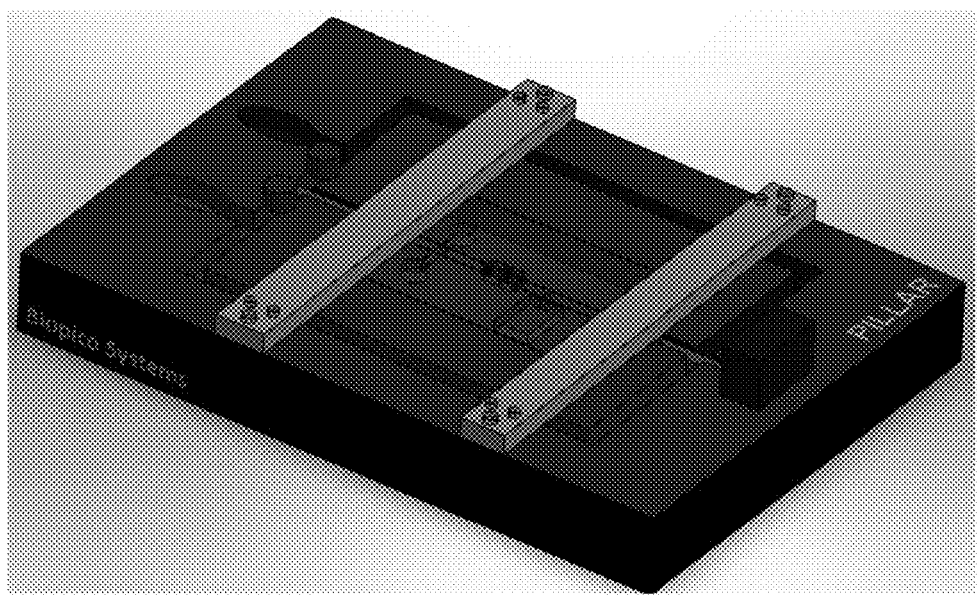
FIG. 26 Fluidic manifold for holding the PILLAR chip and flow based thermal cycling using a set of valves and pumps.
Figure 27A:
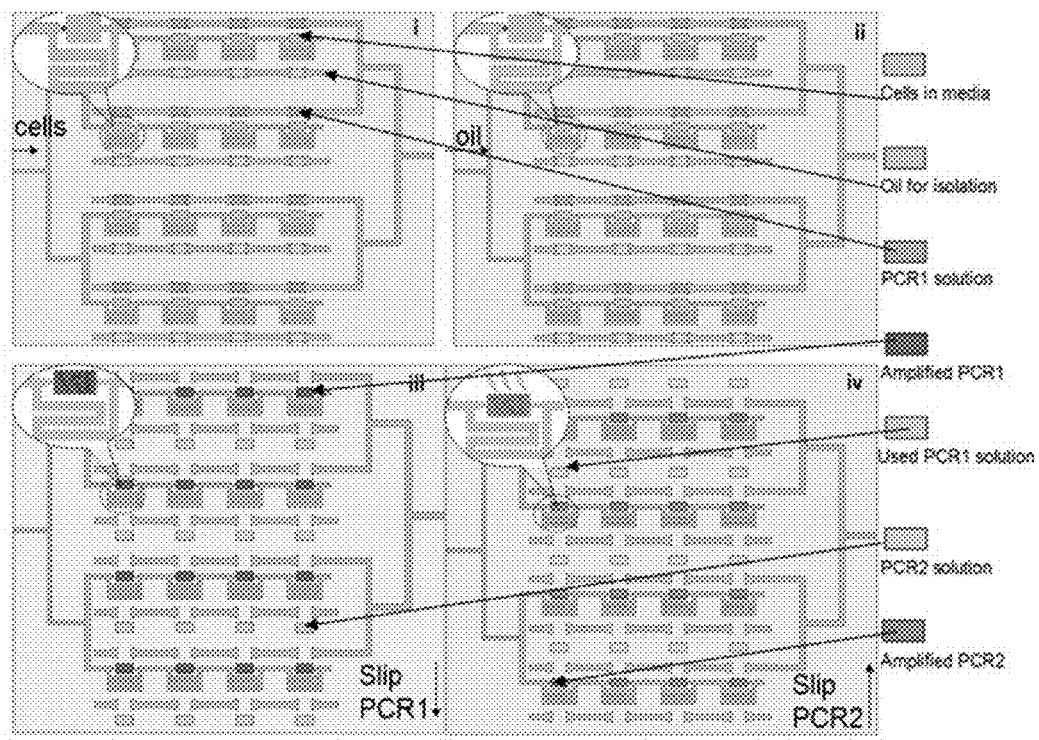
FIG. 27A-27E The picoreactor system in slip and lock platform. The operation steps are (i) Flow of cells for trapping and valving of single cells (ii) flow of oil to encapsulate the single cell in a picoliter volume compartment (iii) Flow of cell lysis/PCR master mix solutions (iv) Slipped chip to flow the add the reagents for PCR reaction. B. The operation steps are Cell encapsulation with oil flow, Thermal cycling: flow of hot oil, Thermal cycling: flow of cold oil, Real time PCR with fluorescent imaging.
Figures 27B, 27C, 27D, 27E:
Figure 28A:
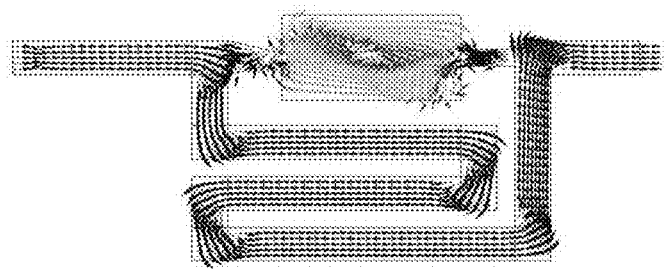
FIG. 28A-28D Results of the flow analysis in a compartment in cell micronozzle cell trap chip using CFD simulations. Velocity profile of the fluid flow. After the encapsulation of single cells with oil. Pressure developed inside the channel due to immiscible flow. CFD results showing single cell trapping and flow blockage for successive cells.
Figure 28B:
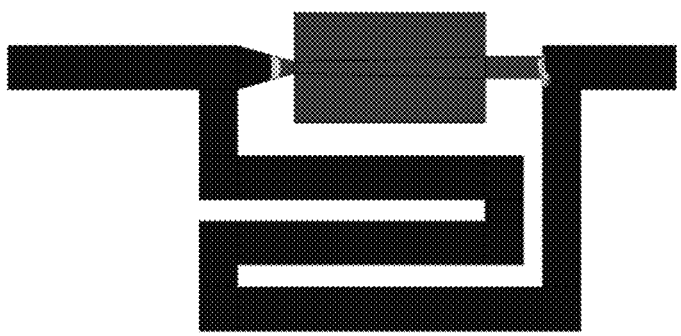
Figure 28C:
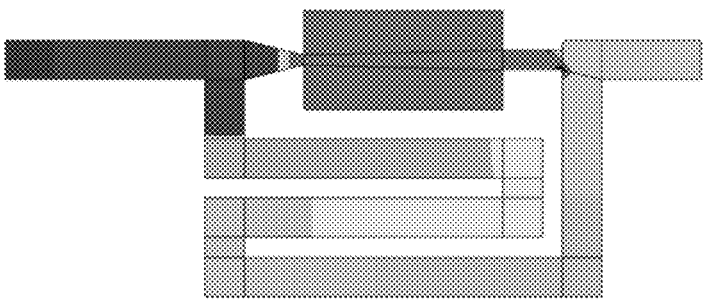
Figure 28D:
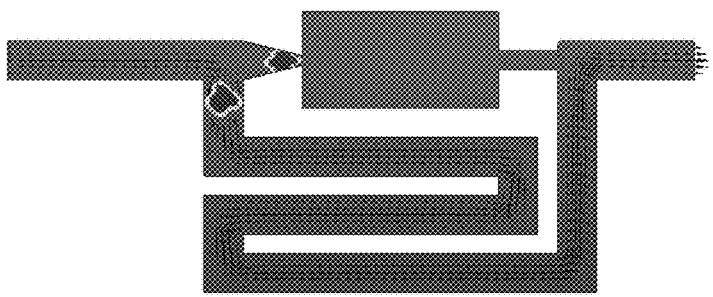

FIG. 22 shows the fluidics diagram of the massively parallel picoreactor chip with inlet splitter channels and outer merger channels for homogeneous cells flow in each compartment. The cells and reagents are flowed from the top inlet. Extra cells or cell clusters adhered weakly near the trap sites are cleaned by the flow at the side inlet. Using CFD simulations, the picoliter reactor forming around trapping sites using immiscible fluids as shown in FIG. 23A-E, is proved. The geometry and dimension of the channel, the flow parameters for aqueous and oil flow, and electrical parameters for the droplet sorting and fusion are optimized and preliminary results of single cell trapping and encapsulation of aqueous fluid using immiscible fluid is shown in FIG. 24A-B Single Cell Trapping Sites:

There are a few mechanisms of trapping sites for single cells. In one case as in shown in FIG. 25, each single cell trapping site is configured by six square micropillars of dimension 5 um×5 um is arranged so that a 10-15 um cell enter and get trapped while the fluid flows away. Additional micropillars are added to increase the volume of PCR mix solution in each reactor site. The $6^{th}$ micropillar at the bottom is added to increase the volume of the encapsulated PCR solution as well as for the smooth formation of droplet. The pitch of the trapping sites are optimized with different pitch in the x and y directions. Lesser the distances the yield of trapping of the cells is better. If the distance is too small there is choking of cells in the channel. If the distances are more the cells freely flow through the device to the outlet and trapping is limited. FIG. 26 shows the fluidic manifold for holding the PILLAR chip and flow based thermal cycling using a set of valves and pumps.

Figure 31A:
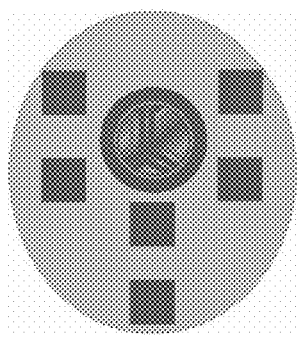
FIG. 31A-31C Single cell diagnostics. Representation of encapsulation of a single cell trapped by a configured array of 6 micropillars. Picoreactor droplet is coupled with EWOD to move the single cell encapsulated droplet for further serial processing. In-situ electrophoresis after PCR amplification in gel medium using a pair of electrodes fabrication on the bottom glass substrate.
Figure 31B:
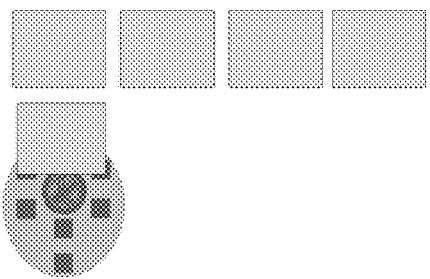
Figure 31C:
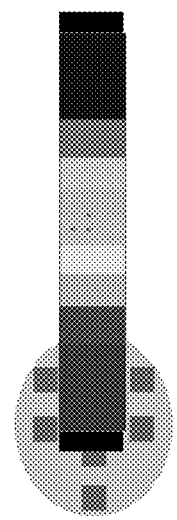

In another method each single cell trapping site is configured by a 5 um nozzle in the microchannel and many such trapping sites are connected in series and parallel throughout the channel as shown in FIG. 27A-E. The single cell trapping sites offer blockage to the flow and successive cells in the direction of the trapped cell. The cells are trapped as they pass through the lower flow resistance or shorter channel. The trapped cells are valved so that successive cells flow through the longer channel as shown in FIG. 28A-D. The number of the trapping sites in series and parallel are optimized with the calculation of the pressure due to the flow of oil and the pump used. The sample with disaggregated cells is loaded into the cell inlet in the microfluidic chip and is split in to many channels using binary splitters. The cells are equally split in all the splitter channels. The cells from splitter channels enter in to the trapping sites and finally merge in binary merger channels to the outlet. The number of cells exiting the outlet is the difference of the cells at the inlet and the number of cells trapped. In a 1"×3" area, ~10000 sites can be accommodated along with other channels for fluidic delivery. FIG. 31A-C shows a single trapping site (a), possible electrophoresis after PCR experiments (b), and picoreactor droplet is coupled with EWOD to move the single cell encapsulated droplet for further serial processing (c).

Splitter/Merger Channels to Compartments:

The sample with disaggregated cells and PCR solution is loaded into the cell inlet in the microfluidic chip and is split in to many channels using binary splitters. The cells are hydrodynamically flowed along with PCR master mix and primers. The cells are equally split in all the splitter channels. The cells from splitter channels enter in to the trapping site compartments in a parallel fashion. Flow of fluid and cells enter in to serial compartments and finally merge in binary merger channels to the outlet. The number of cells entering the outlet is the difference of the cells at the inlet and the number of cells trapped in micropillar sites.

Compartmentalizing the trapping sites improves the homogeneity of the flow of cells within the trapping sites so that the yield of single cell trapping is improved. Placing the compartments serially in a serpentine channel increases the fluidic resistance of the channel. So the flow of cells in the chip is divided in to many subchannels using binary splitters and the compartments are arranged in a parallel fashion. The maximum number of trapping site in a compartment is limited by the parabolic fluidic flow. Using CFD simulation a maximum of 4 trapping sites are configured in the direction perpendicular to the flow. It is also necessary to add sufficient margin in the compartment in all sides for placing the trapping sites. The number of trapping sites on the direction of the flow is limited by the cell density. In a 10 mm×10 mm area, ~10000 sites can be accommodated.

Figure 29A:
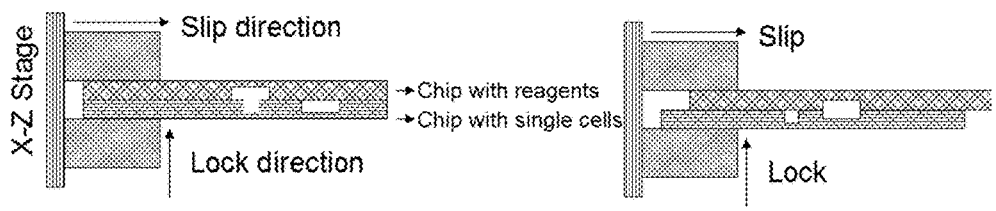
FIG. 29A-29B Schematics of mechanical system for modified slip chip operation using 'slip and lock' stage movement during fluidic delivery. Fluidics operation of slip and lock Chip.
Figure 29B:
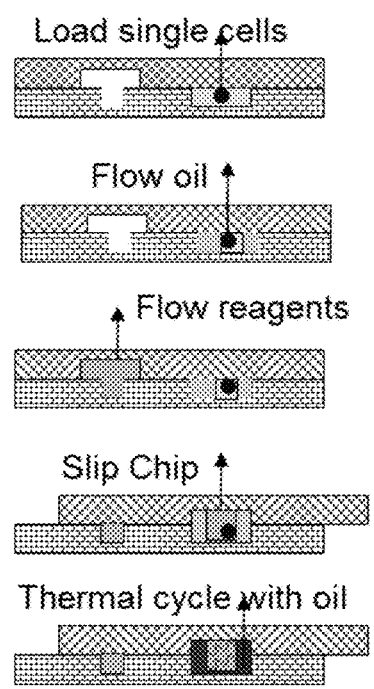

Slip and Lock Chip:

The PCR reagents is be flowed through the top plate and is placed onto the bottom plate in a air tight locked position secured using a Z-stage as shown in FIG. 29A-B or using electromagnetic based locking system. The ducts in the bottom plate were overlapped with the empty wells in the top plate, forming a continuous fluidic path for loading of the sample. The top plate was then moved using a X-stage relative to the bottom plate to align the PCR reagent containing wells in the top plate with the single cell reservoirs in the bottom plate. Once the Slip and Lock Chip is aligned, the PCR reagents and the single cells in both plates are mixed by diffusion. After the mixing, the chip is locked in place using the Z-stage and thermal cycling for PCR is started.

Chip Operation:

The chip is configured to perform five serial steps (1) Microarray spotting of multiple primer pairs, (2) Flow based single-cell trapping using micropillars, (3), Flow of immiscible fluid for forming picoliter reactors (4) convection driven thermal cycling for PCR, and (5) Fluorescence imaging based quantification and deletion analysis. The sample of disaggregated cells along with PCR master mix and PCR solution is loaded into the 'cells inlet' in the disposable microfluidic chip which sits on to the 'fluidic manifold'. The manifold accommodates two oil baths, valves and a pump for oil delivery in to the disposable chip. The sample cells flow is split in to many channels and each single cell is trapped at the micropillars trapping sites. The trapped single cells is encapsulated by flowing oil at RT from cold bath and the oil flow front goes around the micropillars as shown in the CFD simulation. The encapsulated reactor includes single cell, spotted PCR primers and encapsulated PCR master mix with lysing buffer and enzymes. In order to perform PCR thermal cycling oil from isolated hot and cold baths is heated at temperatures 95° C. and 50° C. and is circulated into the entrapped droplets alternately using the pump. Using CFD simulations it is understood that the sealed picoreactors locked at the micropillar sites is immobile with temperature or pressure effects. A heating rate of 1° C./ms and a cooling rate of 2° C./ms are expected during the thermocycling with the circulation of oil. The fluorescence detection system includes a tungsten-halogen/mercury lamp as an excitation source and a CCD detector with an XY stage. After loading the cells and reagents, the chip is operated automatically using Labview software through NI-DAQ interface for final fluorescence analysis of the multiplexed PCR.

System Integration: The system includes a flow device, fluorescence detection, thermal cycler, and software control systems. The flow device is facilitated with Pico syringe pumps (Harvard Apparatus, MA) for delivering fluids into the channel with a constant flow rate between 10 μl/min and 100 nl/min. The PCR is performed using an externally applied programmable Peltier heater. A Peltier heating element (Melcor) controls the nanodroplet temperature between 30 and 95° C. A heating rate of 6-8° C./s and a cooling rate of 2-4° C./s are expected. The timing of the thermal cycling (94° C., 60° C., and 72° C.) is also controlled by the software. The fluorescence detection system includes a tungsten-halogen lamp as an excitation source and a CCD detector (Spectral Instruments Inc., Tucson, Ariz.). Various optical filters are used to accommodate for different fluorescence dyes. The common dyes are FAM, VIC, TAMRA, SYBR Green, JOE, etc. The wavelengths of excitation light are 470 nm, 490 nm, 530 nm, and 635 nm. Since the fluorescence signal is amplified, the CCD has sufficient sensitivity for fluorescence detection. If the array area is too big (>1 cm$^2$) for single illumination, a scanning mechanism is facilitated for multiple illuminations.

Figure 30:
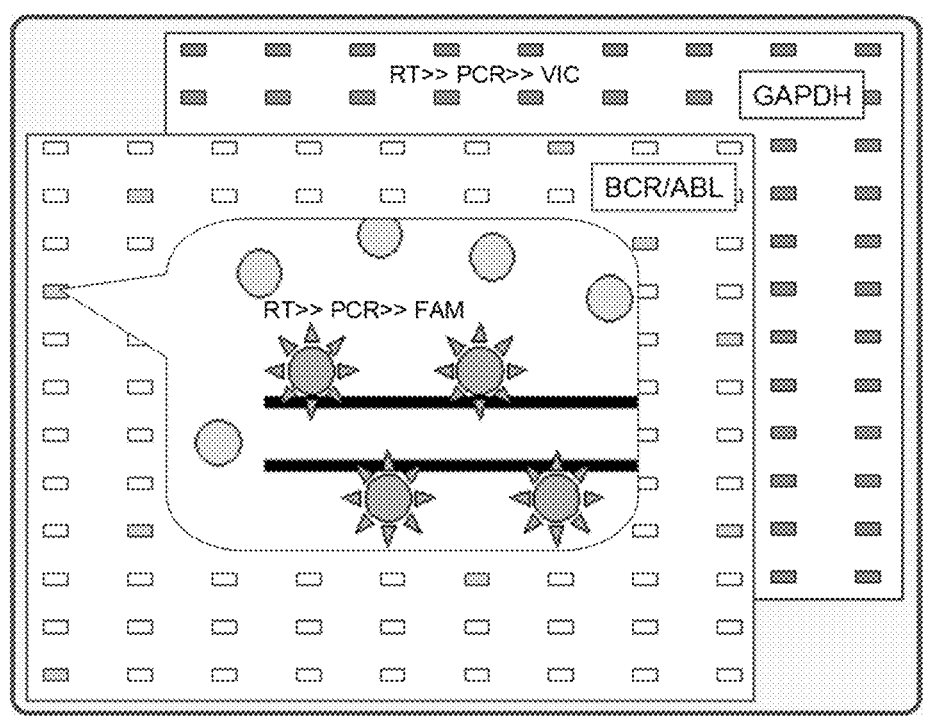
FIG. 30 Digital output for bcr-abl rearrangement detection and positive control (GAPDH).

All the components are programmed using Labview software through NI-DAQ interface. After loading the cells and reagents, the chip is operated automatically for single-cell encapsulation, generating PCR samples, performing temperature control for PCR cycles and final fluorescence analysis of the PCR data. Diagnostics and prognostics analysis through copy number variation are performed using multiple single cell PCR results. A diagram showing the diagnosis of diseases using fluorescence signal with highlighted positive samples is shown in FIG. 30.

Post-Processing of Docked Picoreactor:

Using 'electrowetting on dielectric' (EWOD), the docked picoreactors in trapping sites with single cell encapsulation can be moved for further serial or multistep processing. In order to accomplish the movement of such droplets, EWOD electrodes assembly is laid on the bottom layer of the chip. Further by replacing the oil by a gel medium electrophoresis (with electrodes on glass plate) can be perform after the PCR reaction as shown in FIG. 31C.

Programmable Array of Living Cells

The purpose of this proposal is to develop and commercialize a microfluidic Programmable Array of Living Cells (PAL) for Combinatorial Drug Screening. The overall goal in PAL innovative technology is to demonstrate a low cost, high throughput, multiplexed, automated, integrated, passive, scalable, portable system for cancer therapeutics. The PAL chip can be fabricated for combinatorial fluidics for 16×16 cell based assay reactors. This chip can enable us to perform 2 drugs at 16 concentration or 4 drugs at 8 concentrations for combinatorial drug screening. In this PAL system, ~100 cells are captured by cup shaped pillars and are encapsulated by immiscible fluids as virtual wall in order to isolated different reactors for cell growth monitoring under the influence of drug cocktails. The PAL system (as shown in FIG. 32A-K) is configured to perform four serial steps (I) Flow of cells to fill the 'cup' shaped reactor (II) Flow of buffer for cells cleanup and flow of combinatorial drug. (III) Flow of oil to form cells encapsulated reactors (IV) Cell culture with florescence imaging based cell growth monitoring.

In the single layer pillars chip, the immiscible fluid is very close to the cells. The immiscible fluid, fluorinert is biologically inert and may not interfere with the cell membrane. However, an alternate geometry, as in FIG. 32L, with double layer pillars with cells found only in the inner layer in the 24-72 hours of experiment is presented. The inner layer pillars can be fabricated with smaller (~5 um) spacing while the outer pillars can be fabricated with larger (10-20 um) so that the cells are captured only in the inner compartment. The outer layer pillars can encapsulate sufficient cell media/nutrition for continuous culture for several days. Another feature is an overflow "cup" arrangement for the cells at the top of the inner layer pillars. The gap between the funnel and the cup can be optimized to avoid any clogging of cells. This system can ensure that equal amount of cells can be captured in each reactor.

Example 1: IPSC Sorting for Stem Cell Therapy

The derivation of patient-specific reprogrammed somatic cells makes immunologically compatible stem cell replacement strategy very attractive for several applications such as spinal cord therapy. In potential therapeutic applications, the cell populations relevant for therapy can be electrically excited and the resulting transmembrane ion currents are measured using an array of surface microelectrodes along the direction of the flow. The electrical current measurements in response to electrical stimulation for differentiated states of the cells are built up as electrical signatures for real time comparison and sorting. Since these transmembrane ion currents are measured non-invasively to sort the differentiated cells based on these field potential markers, the sorted cells are highly viable for therapeutic applications. The iPSC line to be studied can be derived from fibroblast sample SC-140 cells. These cells are maintained in StemPro medium on Matrigel-coated plates. The cells are diluted to make a concentration of 2,000 cells per L before using the OFFSET system. These cells are differentiated into neural stem cells, neurons, and glia and after the differentiation, the cells are maintained in appropriate media. The cells are non-enzymatically removed from the plates and immediately introduced into the microfluidic device for sorting. All of the typical criteria needed for clinical cell production can be incorporated into such a process, including donor screening, raw materials sourcing, vendor qualification, process documentation, and assay and process qualification. In this approach, each step of the process must meet its own criteria such that the trajectory from starting material to final product is sufficiently well-characterized that a full characterization of the final product becomes unnecessary.

Example 2: Diagnostics of Cancer

The analysis of heterogeneity in individual tumor cell represents a major step in developing a precise molecular signature of a patient's cancer which leads to therapies tailored to individual patients, an important objective for new oncology drugs. At such single cell level, preamplification of the entire mRNA library to analyze a multigene reverse transcription-PCR panel without compromising the sensitivities of individual marker genes is required. Circulating tumor cells (CTCs) that circulate in the bloodstream alongside normal cells represent a "real-time" biopsy with a surrogate source of tissue in cancer diagnosis and prognosis. The inhomogeneities in the tumor cells and their flow in to blood stream require interrogation of the individual tumor cells and comparison of individual CTCs' expression levels. The ability to quantify and profile the gene expression of CTCs allows improved biological characterization of cancer diagnostics in real time and expedite the development of effective patient-specific therapies. Automated enumeration and characterization of multigenes in circulating tumor cell (CTC) from whole blood have widespread implications in the prognosis and diagnosis of cancer. Furthermore, with the ability to multiplex in a massively parallel fashion, several genes can be screened simultaneously and each panel can also contain desired positive and negative controls. Assays to detect cancer cells in blood have been used clinically to provide prognostic and theranostic information and to test for minimal residual disease. This system has the capacity to process thousand of individual cells; detect circulating tumor cells based on multiplexed PCR results; and analyze the presence or absence of the multiple genes. The presence of circulating tumor cells in the blood can be detected at the single cell level in a population with thousands or more cells by applying single cell PCR assays using expressed mRNA or micro RNA and Philadelphia chromosome positive acute lymphoblastic leukemia (Ph+ALL) are characterized at the molecular level by the bcr-abl fusion transcript. The early detection of mutations in the Bcr-Abl fusion tyrosine kinase by SC-PCR in a cell population may allow timely treatment intervention to prevent or overcome resistance.

Example 3: Diagnostics Using Clinical Blood Samples

Diagnostics using clinical samples is important for routine and non-invasive testing of patients undergoing therapy. For example, Hepatitis C virus (HCV), is a major cause of chronic liver disease, with an estimated 200 million people affected worldwide. Despite recent success after the introduction of combination therapy with interferon (IFN)-α and ribavirin, resistance to antiviral therapy remains a serious problem in the management of chronic hepatitis C. The absence of HCV in the serum of patients by the end of treatment, does not exclude future viremia. The most extrahepatic site for the virus is peripheral blood mononuclear cells (PBMC) and these cells are considered as a potential reservoir of HCV infection. The patient might still be a source of infection to others and so it is strongly encouraged to test for HCV in PBMC to detect lack of response to treatment and persisting infection. Ultrasensitive and specific non-invasive and risk-free monitoring systems that measure very low levels of HCV in blood have been of greater significance for diagnostics and prognostics. The programmable microarray based single cell diagnostics system performs rapid, sensitive, specific and reproducible quantitative monitoring of HCV RNA in PBMCs. This new technology featured by processing very minute amount of samples and reagents has the potential to detect wide variety of liver diseases simultaneously in the frequency domain by digitally analyzing statistically significant samples. The system is useful not only for the diagnostics but also for therapeutics and discovery of new vaccine which has also been hampered by the great heterogeneity of the HCV genome.

Example 4: Diagnosis of Infectious Diseases

Diagnostics of infectious diseases requires and automatic one touch analysis of blood sample or other cells. Precise molecular analysis on single cells from a large population of cells led to the enumeration of cells with specific genes. For example HIV/AIDS diagnosis can be performed by analysis of single PBMC cells for the presence or absence of cell-associated HIV viral genomic RNA and the mRNA of β-actin. Researchers often purify DNA from blood samples prior to performing PCR because it is believed that blood constituents and the reagents commonly used to preserve blood samples (e.g., anticoagulants) interfere with PCR. But in the case of single cell PCR such purification process is not required and high throughput such PCR reactions can be used for the enumeration of CD4 cells which are specifically targeted and destroyed by HIV. A healthy person's CD4 count can vary from 500 to more than 1,000. Even if a person has no symptoms, HIV infection progresses to AIDS when his or her CD4 count becomes less than 200. Prompt diagnosis and treatment can reduce or delay the onset of some serious complications, such as opportunistic infections, and can improve quality of life. In some cases, rapid treatment with medication can prevent the development of HIV/AIDS after exposure to the HIV virus. Normal PBMC and human immunodeficiency virus (HIV) type-1 infected PBMC cells can be distinguished in RT-PCR. The mRNAs released from the cell are reverse transcribed into cDNA using Sensiscript™ Reverse Transcriptase in the enzyme mix.

Example 5: Diagnostics of Prenatal Diseases

The system is used for various genetic diseases or syndrome at prenatal diagnosis. For example, muscular dystrophy refers to a group of more than 30 genetic diseases that involve mutations in any of the thousands of genes that program proteins critical to muscle integrity resulting degeneration of skeletal muscles towards death. Duchenne Muscular dystrophy (DMD), caused primarily by intragenic deletion or duplications has no treatment as of now and prenatal diagnosis is the most important preventive strategy. DMD alone affect approximately 1 in every 3,500 to 5,000 boys or between 400 and 600 live male births each year in the United States. Detection of a DMD gene mutation is sufficient to establish a diagnosis of DMD and so multiplex PCR method is the best diagnostic tool owing to its characteristics such as specific, accurate, sensitive and rapid. Presently, the prenatal diagnosis of DMD is performed through deletion analysis using DNA extracted following amniocentesis or chorionic villous sampling (CVS). After sampling, CVS are microscopically dissected and after homogenization, DNA is extracted and controlled with multiple polymorphic markers to ensure its fetal origin and to avoid maternal tissue contamination, which could possibly result in inaccurate results. The massively parallel microspatially addressed multiplexed PCR system performs fast frequency domain sample analysis of DMD from prenatal samples at high reliability, accuracy and specificity to validate the clinical efficacy and practical feasibility among high risk pregnancies. The prenatal sample may contain maternal tissue contamination which are eliminated by analyzing multiple single cell PCR analysis. Further, multiple polymorphic markers are employed to ensure its fetal origin in multiplex PCR to analyze prenatal DMD diagnostics. This distinguishes between maternal tissue contamination and CVS cells and confirms the single cell PCR performance for deletions analysis of true CVS cells.

Single-cell multiplex PCR is performed using HotStarTaq™ DNA Polymerase (Qiagen, Valencia, Calif.) following the guidelines for single-cell PCR given in the *HotStarTaq PCR Handbook* (Qiagen). Fluorescent multiplex single cell PCR protocol for different mutations of DMD gene is analyzed. Single cells are analyzed for the presence or absence of the exons 45, 48, 49, 43, 19, 3, 8, 13 and the promoter region of the human dystrophin gene for comparison. The cells loaded in the chip along with lysis buffer and PCR master mix react with the dried primers spots in the chip during the PCR amplification. The cDNA are amplified with fluorescent PCR, and fluorescent signals are detected by the fluorescent scanner.

Example 6: Applications in Biomedical Research

Single-cell PCR has proven to be of enormous use to basic scientists, addressing diverse immunological, neurological, and developmental questions, where both the genome and also messenger RNA expression patterns are examined. Enhancements in sensitivity with SC-PCR permits scientists to investigate changes at the level of a single cell, far below what are needed using traditional methods. The understanding of many biological processes would greatly benefit from the ability to analyze the content of single cells.

The system can be used to screen the gene expression variation of few significant genes for regenerative medicine in large number of single cells. The gene expression profile of Nanog and Oct-4 (positive genes for the undifferentiated state) and Pax6 and Sox1 (positive genes for the differentiated state) from SC-140 iPS cells is used quality iPSC.

The advantage of diagnosing a patient's cancer at the single cell level provides us an approach for early detection of cancer and yield insights into how cancer cells are responding or adapting to therapy. An extended single cell technique predicts the pathways of cancer cells that circumvent current therapies and direct the patient towards alternative treatments more intelligently.

The goal in forensic science is to eliminate uncertainty, using technology to precisely determine identity. Researchers continue to refine and improve forensic methods using single cell analysis with success for both increased sensitivity and cost savings.

Fetal cells can be found circulating in maternal blood. Fetal cells recovered from maternal blood provide the only source for noninvasive prenatal DNA diagnosis. Recently, genetic diagnosis using fluorescent PCR has been applied at the single-cell level for sex or single-gene defect diagnosis Circulating tumor cell levels in blood may serve as a prognostic marker and for the early assessment of therapeutic response in patients with metastatic cancer, and are an independent prognostic factor at primary diagnosis. The presence of circulating tumor cells in the blood can be detected at the single-cell level, by applying single-cell PCR assays.

This technology can be extended to diagnostics of various diseases. Small concentration changes and/or altered modification patterns of disease-relevant components, such as mRNA and/or micro RNA, have the potential to serve as indications of the onset, stage, and response to therapy of several diseases. Current single cell PCR methods use individual cells of interest isolated by micromanipulation or cell sorting. Low abundance mRNA is often lost during cell lysis and extraction process. These methods are extremely labor intensive and require expensive equipment to isolate single cells and perform PCR on each cell. However, to detect rare abnormal cells, a large number of cells must be analyzed spontaneously. There is "no" current method that can process, characterize, and perform qRT-PCR for thousands of single cells simultaneously and quickly in picoliter volume.

Example 7: Smartphone Based Applications

Cancer Diagnostics: Smart phone based diagnostics would help in the detection of drug adverse reaction during cancer therapy. Currently, 60% of patients diagnosed with breast, colon, lung, or ovarian cancer already have cell metastases forming in other locations of their body. In addition to antibodies for cancer cell detection, other mechanisms such as peptides and aptamers are used.

HIV Detection: Smart phone based HIV diagnostics can help in the early detection of HIV in remote villages in such countries by health workers. More than 30 million HIV-infected people live in the developing world, where resources are scarce. To increase access to HIV care and improve treatment outcomes, there is an urgent need for low cost diagnostic tools that could be implemented in developing countries. The device can also be engineered to detect other virulent pathogens, including hepatitis B and H1N1 (swine) flu.

Clinical Diagnostics: Smartphone based clinical diagnostics can be used for archiving and monitoring diagnostics data for several diseases so as to provide health information to patients, physicians and healthcare providers. Several clinical diagnostics panels can be used for routine telemedicine. Detection of C-reactive proteins (CRP) in the blood, a preferred method for helping doctors assess the risk of cardiovascular and peripheral vascular diseases can help in saving the life of many seniors and other patients through smart phone based telemedicine. The number of CRP tests paid for by Medicare tripled from 145,000 to 454,000 (from 2002 to 2004), and it is estimated that those numbers have quadrupled since then.

It is to be appreciated that the present invention has been described hereabove with references to certain examples or embodiments of the present invention but that various additions, deletions, alterations and modifications may be made to those examples and embodiments without departing from the intended spirit and scope of the present invention. For example any element or attribute of one embodiment or example may be incorporated in to or used with another embodiment of example unsuitable for intended use. All reasonable additions, deletions, modification and alterations are to be considered equivalents of the described examples and embodiments and are to be included within the scope of the following claims.

What is claimed is:

1. A spiral microfluidic channel system comprising:
   an inlet for flowing a plurality of cells;
   a primary spiral microfluidic channel coupled to said inlet, said primary spiral microfluidic channel comprising a plurality of pinching regions; and
   a plurality of secondary spiral microfluidic channels for separating said plurality of cells, wherein at least one of said plurality of secondary spiral microfluidic channels has progressively varying widths.

2. The spiral microfluidic channel system of claim 1, wherein said primary spiral microfluidic channel is coupled to at least one of said plurality of secondary spiral microfluidic channels through a plurality of right angled interconnect channels.

3. The spiral microfluidic channel system of claim 1, wherein said primary spiral microfluidic channel has decreasing width from said inlet to an outlet.

4. The spiral microfluidic channel system of claim 1, wherein at least one of said plurality of secondary spiral microfluidic channels has increasing width from said inlet to the corresponding outlet(s).

5. The spiral microfluidic channel system of claim 1, wherein said plurality of pinching regions are periodically disposed along a convex or concave sidewall of said primary spiral microfluidic channel.

6. The spiral microfluidic channel system of claim 1, wherein said primary spiral microfluidic channel is coupled to one of said plurality of secondary spiral microfluidic channels through a first plurality of interconnect channels.

7. The spiral microfluidic channel system of claim 6, wherein said one of said plurality of secondary spiral microfluidic channels is coupled to another one of said plurality of secondary spiral microfluidic channels through a second plurality of interconnect channels smaller than said first plurality of interconnect channels, such that larger cells from said plurality of cells are trapped in said primary channel and smaller cells from said plurality of cells are passed to said plurality of secondary channels.

8. The spiral microfluidic channel system of claim 1, wherein said primary spiral microfluidic channel is configured to separate circulating tumor cells (CTCs) from said plurality of cells.

9. The spiral microfluidic channel system of claim 1, wherein at least one of said plurality of secondary spiral microfluidic channels is configured to separate red blood cells (RBCs) from said plurality of cells.

10. The spiral microfluidic channel system of claim 1, wherein the primary channel consists of abrupt enlargement of the channel with interconnect channels connecting to at least one of said plurality of secondary spiral microfluidic channels.

11. The spiral microfluidic channel system of claim 10, wherein the interconnect channels start in the direction opposite to the director of flow in the primary channel.

12. The spiral microfluidic channel system of claim 1, wherein said primary spiral microfluidic channel and said plurality of secondary spiral microfluidic channels are substantially concentric.

13. The spiral microfluidic channel system of claim 12, wherein the outlets of the substantially concentric spiral microfluidic channels are closed except for the last channel.

14. The spiral microfluidic channel system of claim 12, wherein the substantially concentric spiral microfluidic channels form fractional or multiple turns.

15. The spiral microfluidic channel system of claim 1, wherein expansion structures have increasing widths from inlet to outlet throughout the spiral channels.

* * * * *